United States Patent [19]

Ishihara et al.

[11] Patent Number: 5,791,345
[45] Date of Patent: *Aug. 11, 1998

[54] NON-INVASIVE BLOOD ANALYZER

[75] Inventors: Ken Ishihara; Hiroshi Yamamoto; Mitsuru Watanabe; Kaoru Asano; Akio Suzuki; Yasunori Maekawa; Yasuhiro Kouchi. all of Hyogo, Japan

[73] Assignee: Toa Medical Electronics Co., Ltd., Hyogo, Japan

[*] Notice: The term of this patent shall not extend beyond the expiration date of Pat. No. 5,598,842.

[21] Appl. No.: 565,046

[22] Filed: Nov. 30, 1995

Related U.S. Application Data

[63] Continuation-in-part of Ser. No. 296,897, Aug. 29, 1994, Pat. No. 5,598,842.

[30] Foreign Application Priority Data

Nov. 30, 1994 [JP] Japan .................................. 6-297335
May 26, 1995 [JP] Japan .................................. 7-128420

[51] Int. Cl.$^6$ ............................... A61B 5/00; A61B 1/04
[52] U.S. Cl. ................................ 128/637; 356/39
[58] Field of Search ........................ 128/633, 637, 128/664, 665; 356/39

[56] References Cited

U.S. PATENT DOCUMENTS

| | | | |
|---|---|---|---|
| 4,453,266 | 6/1984 | Bacus | 382/6 |
| 4,974,094 | 11/1990 | Morito | 358/225 |
| 4,998,533 | 3/1991 | Winkelman | |
| 5,080,098 | 1/1992 | Willett et al. | 128/633 |
| 5,240,006 | 8/1993 | Fujii et al. | 128/665 |
| 5,279,297 | 1/1994 | Wilson et al. | 128/633 |
| 5,348,003 | 9/1994 | Caro | |
| 5,394,199 | 2/1995 | Flower | 128/633 |
| 5,437,274 | 8/1995 | Khoobehi et al. | 128/664 |
| 5,598,842 | 2/1997 | Ishihara et al. | 128/637 |

FOREIGN PATENT DOCUMENTS

| | | | |
|---|---|---|---|
| 3619442 | 12/1987 | Germany | 128/633 |
| 4161915 | 6/1992 | Japan | |
| 92/03965 | 3/1992 | WIPO | 128/637 |
| A9313706 | 7/1993 | WIPO | |

OTHER PUBLICATIONS

Ieee Engineering in Medicine and Biology, vol. 13, No. 3, Jul. 1994 New York, pp. 319–325.

Fagrel et al "Capillary Flow Measurement in Human Skin" in *Clinical Invest. of the Microcirculation* pp. 23–33, 1987.

*Primary Examiner*—Jennifer Bahr
*Assistant Examiner*—Eric F. Winakur

[57] ABSTRACT

A non-invasive blood analyzer is intended to capture images of a prescribed volume of blood in a blood vessel in a non-invasive manner and with a good contrast without collecting blood from a living body. The non-invasive blood analyzer includes a light application device for illuminating a detection region of vessels contained in a part of a living body, an image capturing device for capturing images of the detection region illuminated by the light application device, and an analyzer for analyzing blood components contained in the detection region by processing the images captured by the image capturing device. The image capturing device includes an object lens for converging the reflected light from the detection region. The light application device illuminates the detection region at an incident angle larger than an aperture angle of the object lens with respect to the detection region to provide dark-field illumination.

15 Claims, 21 Drawing Sheets

NON-INVASIVE BLOOD ANALYZER

CROSS-REFERENCE TO RELATED APPLICATION

This application is a continuation-in-part of application Ser. No. 08/296,897 filed on Aug. 29, 1994, now U.S. Pat. No. 5,598,842, the entire contents of which are hereby incorporated by reference.

FILED OF THE INVENTION

The present invention relates to an apparatus for analyzing blood in a non-invasive manner, and more particularly to an apparatus for analyzing blood components necessary for a hematology test by optically measuring blood flowing through vessels in a living body.

RELATED ART

The items of hemotology test such as the number of blood cells, hematocrit, hemoglobin, and corpuscular constant (mean corpuscular volume: MCV, mean corpuscular hemoglobin: MCH, and mean corpuscular hemoglobin concentration: MCHC) are extremely important for the diagnosis of diseases and the treatment thereof. Such items are most frequently used in a clinical test of patients.

Analysis of blood components is extremely important for the diagnosis of diseases and the treatment thereof. Generally, such a hematology test involves collecting blood from a living body to analyze a sample thereof with an analyzer. However, the collection of blood from the living body causes considerable pain to the living body. Also, since the collected blood is usually transported, before analysis, to a clinical laboratory where an analyzing apparatus is placed, it is impossible to conduct a real-time hematology test during diagnosis. Moreover, the above method is always accompanied by a fear that needles for blood collection might cause an accident due to erroneous injection when they are used for collecting blood from a different living body infected with an infectious disease such as hepatitis and AIDS.

Thus, a demand has been made for many years that an apparatus be developed that allows practitioners to perform a blood test in a non-invasive manner. When such a blood analyzer is installed beside the bed on which the living body is laid, the practitioners can monitor real-time conditions thereof on the spot without difficulty.

Examples of the widely known prior art relating to such apparatus include a video microscope which applies light to an observation site on a skin surface of a living body to capture a video image thereof (static image) at a shutter speed of about one thousandth of a second and identifies discontinuous points in the blood stream that move one by one on the static image, and an analyzer providing a video camera equipped with a high-speed shutter which captures images of red blood cells in the conjunctival capillary blood vessels in an eyeball (see, for example, Japanese Unexamined Patent Publication No. HEI4(1992)-161915 and U.S. Pat. No. 4,998,533).

By the way, the speed of blood flow is about five mm to tens of mm per second. When images of red blood cells are captured at a shutter speed of one thousandth of a second like in the prior art assuming that the blood flows at a rate of 10 mm per second, red blood cells move by the distance equal to the diameter thereof thereby generating a shift in the image by the diameter.

Furthermore, red blood cells adjoin each other in blood vessels with a space of the diameter thereof or less therebetween and almost all the red blood cells overlap each other in the image due to the shift in the image thereof. Consequently, the above Japanese prior art is far from allowing examiners to quantitatively measure the above test items through the morphological analysis of blood cells and the counting of the number thereof from captured images.

On the other hand, the analyzer disclosed in U.S. Pat. No. 4,998,533 captures conjunctival capillary blood vessels in an eyeball with the video camera. However, the focus of the video camera is relatively shifted at all times with respect to the captured portion of the eyeball because of a slight motion inherent in the eyeball. Thus, it is very difficult to repetitively capture the same region of the captured portion thereof with the video camera. It is impossible to mechanically stop the slight motion of the eyeball by closely contacting some object to eyeballs because the eyeball might be damaged. Furthermore, U.S. Pat. No. 4,998,533 describes counting the number of RBC and measuring HCT, MCV and MCHC, but it describes no procedure for measuring these values.

Since the intensity of light diffused at skin surface is strong when light is applied to a living body, an apparatus such as described above does not allow images of a blood vessel (blood) to be captured with a good contrast, rendering it difficult to conduct a quantitative analysis from the obtained images.

SUMMARY OF THE INVENTION

The present invention has been conceived in view of the above circumstances, and an object of the invention is to provide an apparatus which can analyze blood in a non-invasive manner by capturing, with good accuracy and contrast, images of blood and blood vessels in a living body followed by analyzing blood components from the captured images.

The aforementioned and other objects of the present invention are fulfilled by providing a non-invasive blood analyzer comprising: light application means for illuminating a detection region in a blood vessel contained in a part of a living body; image capturing means for capturing images of the detection region illuminated by the light application means; and analysis means for analyzing blood components contained in the detection region by processing the images captured by the image capturing means, wherein the image capturing means includes an object lens for converging the reflected light from the detection region and the light application means illuminates the detection region at an incident angle larger an aperture angle of the object lens with respect to the detection region to provide a dark field illumination.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
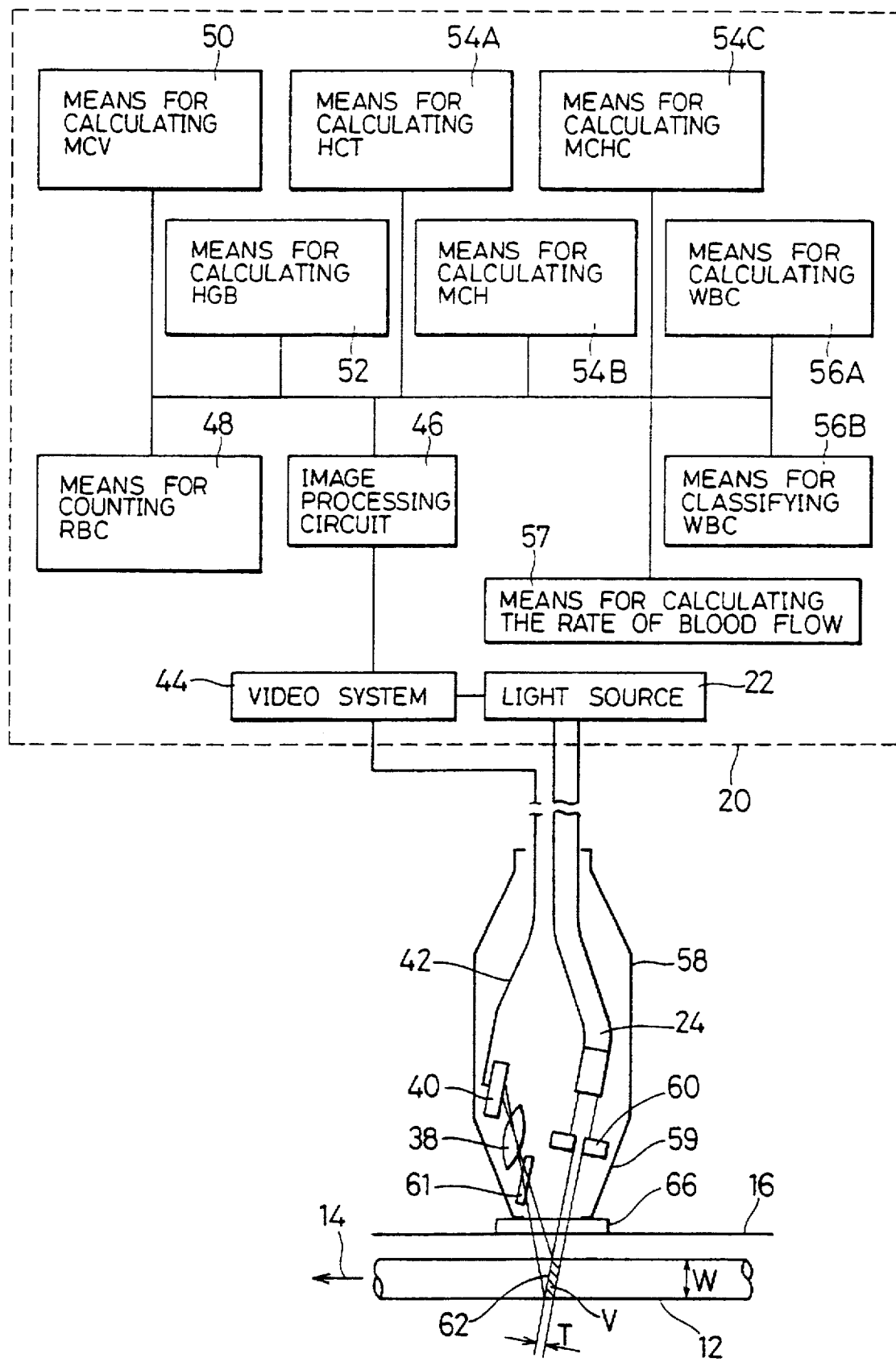
FIG. 1 is a view illustrating the structure of embodiment 1 of the present invention.

The blood analyzer of the present invention is characterized by analyzing blood in a living body in a non-invasive manner. Preferably, the living body is that of mammals including human beings. The term "blood components" as used herein refers to blood cells such as red blood cells (erythrocytes) and white blood cells (leukocytes), and to components in a living body such as hemoglobin, bilirubin, and glucose.

The part of the living body refers to a portion having blood vessels below the skin, such as a lip, a finger, an earlobe, and an eyeball. Preferably, the part of the living body is a portion which will not be easily damaged by light from outside or a contacting object, such as a lip, a finger, and an earlobe. The detection region in the blood vessel refers to a predetermined region of the blood vessel that is really present in the living body. Namely, in this particular invention, the predetermined region is referred to as a detection region.

This region may be partitioned with two parallel planes traversing orthogonally or diagonally relative to the direction of blood flow. Preferably, the distance between the parallel planes may be about 10 to 20 microns.

On the other hand, the thickness of the subject blood vessels is not limited, but capillary arteries and veins are preferable to produce a good result in reproduction of the detected state. Incidentally, blood cell information obtained in capillary arteries and veins can be translated into information on thick vessels (medium-size or large arteries and veins).

The light application device of the present invention allows illumination light to be directed to the detection region from the outside of the object lens of the image capturing device. In other words, the illumination light illuminates the detection region at an incident angle larger than an aperture angle of the object lens with respect to the detection region. Consequently, since the illumination light reflected at the skin surface of the living body is directed to the outside of the aperture angle of the object lens, thus failing to reach the image capturing device, the contrast of the image captured by the image capturing device is greatly improved.

As the light application means of the present invention, either a continuous or intermittent light source may be used; the continuous light source that continuously applies light to the detection region may be a laser, a halogen lamp or a tungsten lamp while the intermittent light source that applies light intermittently to the detection region may be a pulse laser (for example, 7000 series manufactured by Spectra-Physics Co., Ltd.), a multi-stroboscope (for example, DSX series manufactured by Sugawara Laboratories, Inc., Japan), or a Xe flash lamp.

Preferably, the continuous light source may incorporate an optical shutter therein to be used as an intermittent light source. As the optical shutter, a known acousticoptic or electrooptic modulator may be used. Incidentally, the light application (flickering) duration of the intermittent light source may be set to within the range of one ten thousandth to one billionth of a second.

Besides, the light application means may further comprise at least one of an optical fiber, a reflector, a polarizing element, a lens φ, a prism, a slit, and a filter in addition to the above light source. Light emitted from the light source may be directed to the detection region by an appropriate combination of the above device.

Further, the light application means may be constructed with a plurality of light emitting elements disposed around the object lens and a light guiding device for directing the light emitted by the light emitting elements to the detection region. In this case, the light emitting element may preferably be a small and inexpensive element such as a LED (Light Emitting Diode), an LD (Laser Diode), and a SLD (Super Luminescent Diode).

Alternatively, the light application means may be constructed with a plurality of light emitting elements disposed around the object lens, each of the light emitting elements having a different emitting wavelength, a light guiding device for directing a light emitted by the light emitting elements to the detection region, and a control device for selectively energizing the light emitting elements each having a different emitting wavelength.

In this case, the light emitting element having a different emitting wavelength may preferably be an element such as a blue LED (with peak wavelength at 450 nm), a green LED (with peak wavelength at 560 nm), and a red LED (with peak wavelength at 660 nm) corresponding to light absorption characteristics of the object whose images are to be captured.

For example, oxyhemoglobin shows high absorptivity at around 450 nm and 560 nm and low absorptivity at 660 nm. Therefore, oxyhemoglobin concentration can be determined by illuminating the detection region with a red LED and either one of blue and green LEDs followed by analyzing the obtained differential image.

On the other hand, bilirubin shows high absorptivity at around 450 nm and low absorptivity at 560 nm. Therefore, images of bilirubin can be captured by illuminating the detection region with a blue LED and a green LED followed by analyzing the obtained differential image.

Here, the control means for selectively energizing the light emitting elements each having a different wavelength may be, for example, a power circuit equipped with a switching function capable of selectively supplying electric power to the light emitting elements each having a different wavelength.

As the image capturing means of the present invention, a general CCD image sensor for visible light, infrared light, and ultraviolet light may be used. In particular, a CCD image sensor provided with an electronic shutter having a shutter speed of one ten thousandth of a second or more is preferably used. Examples of such a CCD image sensor include XC-73CE and XC-75/75CE (provided with a variable shutter having a maximum shutter speed of one five hundred thousandth of a second) both manufactured by Sony Corporation in Japan.

Furthermore, the image capturing means may optionally comprise at least one of an optical fiber, a reflector of each kind, a polarizing element, a lens of each kind, a prism, a slit, a filter, and an image intensifier so that an appropriate combination of the above devices allows the reflected light from the detection region to be introduced into the CCD image sensor.

In accordance with the present invention, the light application device and the image capturing device may form one image during one ten thousandth to one billionth of a second of the light application and image capturing process. For example, a red blood cell moving at a speed of 10 mm per second through the vein moves by a distance of one micron during one ten thousandth of a second. A shift in the image of the red blood cell captured with the device of the present invention is equal to 10% of the diameter (10 microns) of a red blood cell.

Even in the presence of an image blur of such a degree, morphological analysis of blood cells in a blood vessel and the counting of the number thereof are experimentally proved to be possible. When one image is formed in one hundred thousandth of a second, the image blur can be suppressed to one tenth thereof (1% of the diameter). When one image is formed in one millionth of a second, the image blur can be suppressed to one hundredth thereof (0.1% of the diameter). Consequently, the accuracy in the morphological analysis of blood cells and the counting thereof improves with shortening of the time required for forming one image.

However, the amount of light received by the image capturing device reduces as the time for forming one image is shortened. Thus, the amount of light emitted from the light application device and/or the light sensitivity of the image capturing device need to be increased. Preferably, one image formation time ranges from one ten thousandth to one billionth of a second. More preferably, the time ranges from one fifty thousandth to one two hundred thousandth of a second in this application.

Then, in order to form one image in time ranging from one ten thousandth to one billionth of a second, preferably light application means having an intermittent light source and image capturing means including a CCD image sensor are combined, or light application means having a continuous light source and image capturing means including a CCD image sensor with an electronic shutter are combined. When the analysis device analyzes blood components by detecting a hemoglobin, bilirubin or glucose concentration in blood, the time for forming one image is not always so shortened. Furthermore, the light application device and the image capturing device are preferably constituted to capture a plurality of images in a predetermined cycle so that the analysis device can analyze the morphology of blood cells including their color tone and/or count the number thereof based on the plurality of images.

Incidentally, the image capturing device may further provide a recording device for recording the captured images such as, for example, an image memory or a video tape recorder.

Generally, the number of blood cells as an item of hematology test is calculated in terms of the number per blood volume. It is necessary to know the volume of the detection region for the calculation.

The volume (capacity) of the detection region is calculated in the following manner.

(1) The volume is calculated from an area of the captured image, a depth to which the image capturing device can capture images (depth of focus) and a magnification ratio thereof.

(2) Light is applied to a detection region of predetermined volume in a blood vessel with the light application device so that images of the region to which the light is applied are captured.

(3) The volume of the detection region is calculated by measuring the internal diameter and length of the imaged blood vessel at the detection region.

In accordance with the above method (2), when a slit light is directed to a blood vessel in the vertical or diagonal direction relative to the blood flow with the light application device in such a manner that the blood vessel is sliced into a thin disk with the slit light, the capturing device captures the sliced region from the direction of the cross section thereof. In this manner, the dynamic mechanism of blood cells that flows through the blood vessel can be captured from the direction of the blood flow. Thereby, the volume of the detection region can be calculated from the product of the area of the cross section of the blood vessel and the slit width thereof.

In the capturing of the cross section of the blood vessel, preferably the capturing surface of the capturing device is disposed so as to be focused on the overall surface of the cross section by the swing and tilt photography (since the swing and tilt photography is a known art, detailed description thereof is not given here).

The analysis device according to the present invention preferably provides an analog and/or digital mode image processing device selectively having functions such as each kind of filter, γ(gamma) correction, interpolation, jitter correction, color tone conversion, color balance correction, white balance and shading correction.

Furthermore, the analysis device for analyzing blood components preferably comprises capabilities for calculating the number of red blood cells (erythrocytes) and/or white blood cells (leukocytes); for calculating a hematocrit value; for calculating hemoglobin (HGB) by analyzing the intensity of reflected light from the detection region; means for calculating the mean corpuscular volume (MCV), the mean corpuscular hemoglobin (MCH), and mean corpuscular hemoglobin concentration (MCHC) based on the morphology of blood cells; for analyzing the morphology of blood cells and classifying thus analyzed blood cells; and for converting blood cell information obtained from arteriolas and veinlets or capillary arteries and veins into blood cell information corresponding to medium-size and large arteries and veins.

The analysis device may also comprise capabilities for analyzing hemoglobin concentration, for analyzing bilirubin concentration, and for analyzing glucose concentration.

The analysis means may be constructed using a digital signal processor (DSP), for example, TMS320C30 manufactured by Texas Instruments, Inc.

Figure 17:
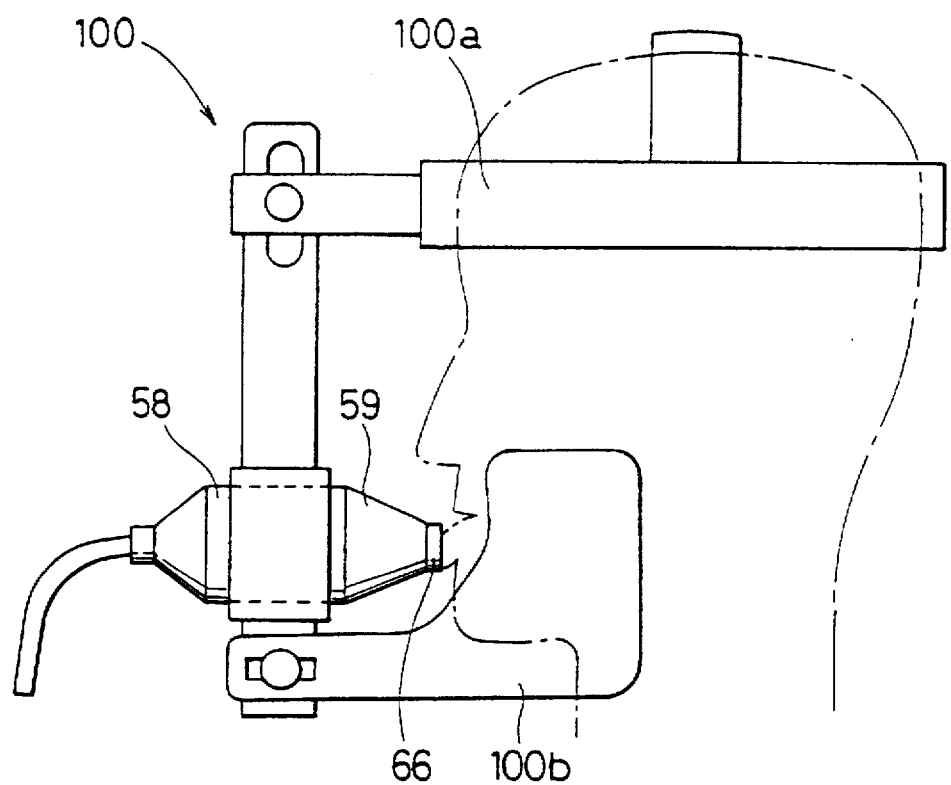
FIG. 17 is a view showing an example in which a probe is attached in an embodiment.
Figure 21:
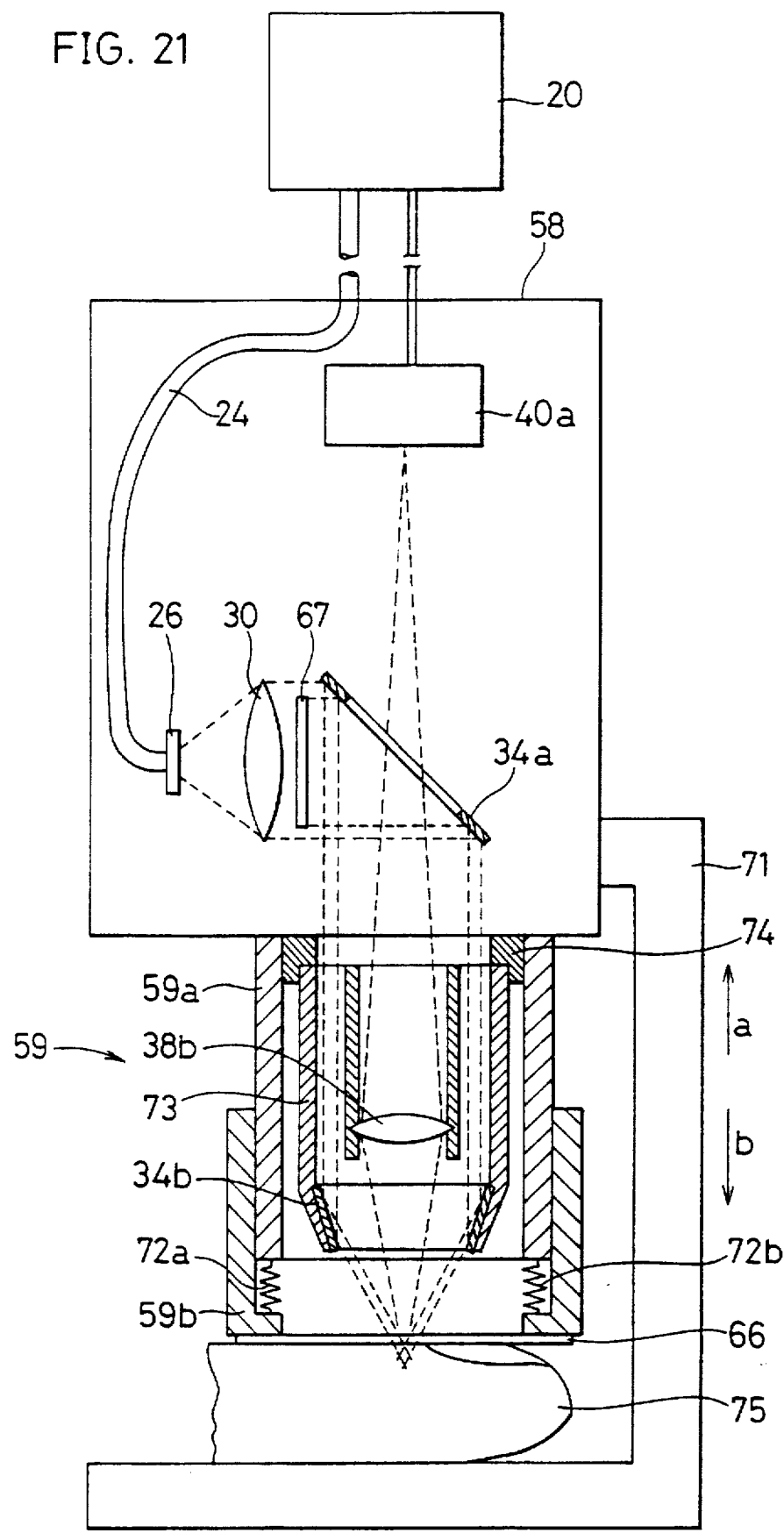
FIG. 21 is a view showing a modification of embodiment 4 shown in FIG. 20.

Desirably, the non-invasive blood analyzer provides a fixing device for relatively fixing at least part of the living body and the image capturing means and a stabilizing device for stabilizing the focus of the image capturing device with respect to the detection region in order to exactly apply the light from the light application device to the detection region in the vessel and clearly photograph the detection region. For this purpose, more preferably, the blood analyzer of the present invention provides an integral or separate fixing device and stabilizing device. The structure of such means can be appropriately designed in consideration of the analyzer and the part containing the detection region. The structure thereof can also be determined in consideration of the configuration and size of the living body portion where the detection region exists. For example, when the detection region is contained in a capillary vessel in a lip, a device as shown in FIG. 17 can be used. In addition, when the detection region is contained in a capillary blood vessel in a finger, a device as shown in FIG. 21 can be used.

However, when the analysis device analyzes blood components by detecting a hemoglobin, bilirubin or glucose concentration in blood, the blood analyzer does not always provide such a fixing device and stabilizing device.

EXAMPLES

The present invention will be detailed in conjunction with the preferred embodiments, which are not intended to limit the scope of the present invention.

Embodiment 1

FIG. 1 is a view illustrating a structure of embodiment 1 of the present invention. As shown in FIG. 1, a light application device for applying light to a detection region V in a blood vessel 12 that exists inside of a skin surface 16 of a living body comprises a light source 22, an optical fiber 24, and a slit 60. Additionally, an image capturing device comprises a CCD 40 provided with one hundred thousandth ($10^{-5}$) of a second electronic shutter, a lens 38, a polarizing filter 61 and a video system 44.

Then, an analysis device which processes images captured with the CCD 40 provided on the image capturing device and which analyzes the morphology and/or the number of blood cells contained in the detection region V comprises an image processing circuit 46, means 48 for counting the number of red blood cells, means 50 for calculating MCV, means 52 for calculating HGB, means 54A for calculating HCT, means 54B for calculating MCH, means 54C for calculating MCHC, means 56A for calculating the number of white blood cells, means 56B for classifying white blood cells, and means 57 for calculating the blood flow rate.

Figure 2:
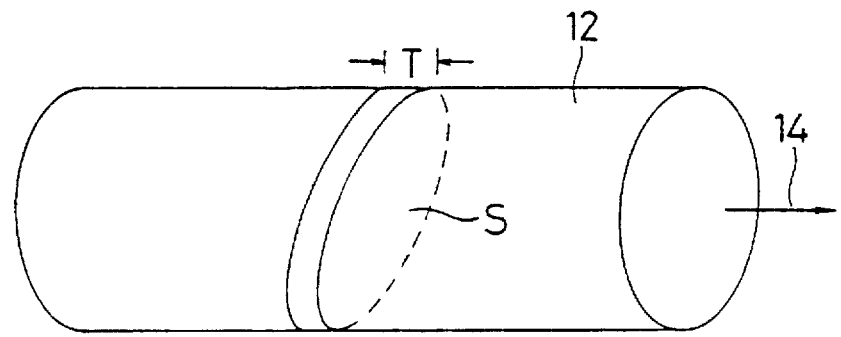
FIG. 2 is a view showing an example of a detection region according to the present invention.

Then, the CCD 40 forms one image frame each time the CCD captures an image of the detection region V irradiated with light at a shutter speed (image capturing time) of one hundred thousandth of a second ($10^{-5}$sec). In this embodiment, as shown in FIG. 2, the light application device forms the thin disk-like detection region V having a cross section S and a thickness T with a slit-shaped beam of light applied to the blood vessel 12 in a direction diagonal with respect to the direction of the blood stream of the blood vessel 12 so as to capture images of blood cells that exist in the detection region V. Incidentally, in FIG. 1, a subcutaneous portion (below the skin 16) of the living body is magnified for convenience.

The light source 22 is accommodated in the main body 20 of the analyzer. The tip of the optical fiber 24, the slit 60, the CCD 40, the lens 38, the polarizing filter 61 are all accommodated in a probe 58. Laser light emitting from the light source 22 is controlled with the slit 60 after coming out of the tip of the optical fiber 24 and is translated into a thin belt-like (slit-shaped) optical beam having a thickness T to irradiate the living body. A transparent plate 66 made of plastic or glass is provided to provide a stable image by allowing a tip 59 of the probe 58 to closely contact the skin surface 16.

When the belt-like (slit-shaped) optical beam traverses the blood vessel 12, a specific region of the blood vessel is irradiated to form a detection region V. The reflected light coming from the detection region V is received at a light receiving surface of the CCD 40 via the polarizing filter 61 and the lens 38. The resulting captured image is recorded in the video system 44 via a transmission cable 42. Here the "swing and tilt" photography technique is used to capture a reflected light coming from a cross section 62 having a thin disk-like configuration. Since the cross section 62, the lens 38, and the CCD 40 are disposed, with respect to the optical axis, at positions that enable the "swing and tilt" photography technique, a clear image is provided with the entire cross section 62 in focus.

The area S of the cross section 62 is determined by dividing the square of the imaging magnification into the area of the captured image of the cross section. Since the thickness T which represents the thickness of the belt-like optical beam is already known from the slit width of the slit 60, the volume of the region V can be calculated.

Furthermore, the volume of the region V may be determined by cutting out the captured image of the cross section with a window having a predetermined area, dividing the square of the imaging magnification into the window area and multiplying the thus given value by the thickness T.

Since the thickness T of the region V is set to a small value, for example, on the order of 10 microns, a probability is not so high that blood cells overlap a flat image captured with the CCD. Even if the blood cells overlap the flat image, it is still easy to differentiate each of the blood cells on the image with the image processing technique.

Incidentally, it is possible to calculate the number of blood cells from one frame of the image as described above. In this embodiment, tens of frames of images to several hundreds of frames of images are continuously captured to enhance the accuracy in the analysis. In other words, although a distribution of blood cells should be essentially determined from a wide scope of blood vessels to calculate each of the above indices based on the determined distribution, it is found that the distribution of blood cells can be determined from a large number of images obtained by the continuous image capturing of the same detection region to statistically calculate each reliable index based on the distribution thus determined.

When an image intensifier provided with a high speed gate is adopted into the image capturing means, a clear image can be obtained even when the amount of light application to the blood vessel is small. Thus the light source may have such a low power that the light application to the living body might not cause a burn thereon.

As shown in FIG. 1, the handling of the optical system can be facilitated by integrally accommodating all the equipment of the optical system in the single probe 58. Thus, images of blood cells can be captured and measured only by placing the tip of the probe 58 on the surface of the skin 16 via the transparent plate 66.

FIG. 17 is a view illustrating a state of measuring a blood vessel in a lip by attaching the probe 58 to an attaching device to fix the probe 58 to a subject. A forehead fixing part 100a fixes a probe attaching device 100 to the forehead of the subject, and a jaw fixing part 100b fixes the probe attaching device to the jaw of the subject. When the probe 58 is allowed to closely contact the lip as a detection region via a stabilizing device, for example, a transparent plate 66 by using the probe attaching device as shown in FIG. 17, the friction of the transparent plate 66 causes the tip of the probe 58 to be fixed on the skin surface of the subject to suppress the fine vibration of the lip portion relative to the tip of the probe 58, thereby stabilizing the focus of the image capturing system and preventing the detection region from mechanically shifting with respect to the image capturing system.

Furthermore, providing the polarizing filter 61 on the light receiving system enables the removal of unnecessary components of scattered light to give a good image having a good contrast. Even if no polarizing filter is mounted on the light application system at this time, the filter on the light receiving system can improve the contrast of the image to a considerable degree. Preferably, the light application system includes a polarizing filter. A method may be used which involves introducing a polarized laser beam through a polarized wavefront protection fiber.

Figure 3:
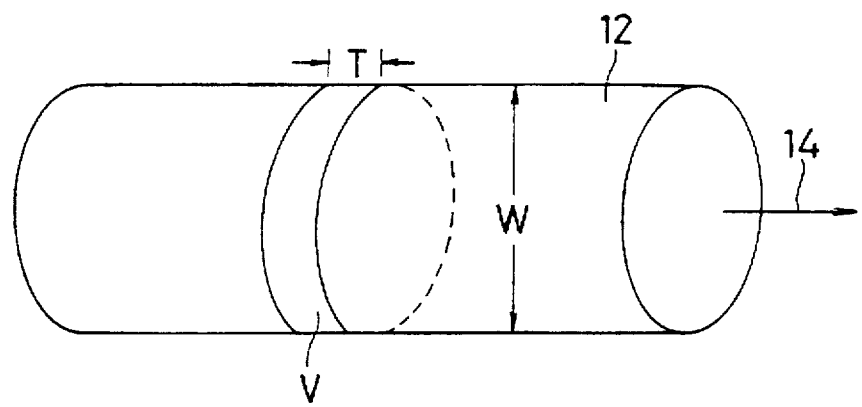
FIG. 3 is a view showing an example of a detection region according to the present invention.

In FIGS. 1 and 2, the volume region V for detection is formed in a disk-like configuration diagonally with respect to the direction of the blood stream through the blood vessel 12. However, as shown in FIG. 3, the region V may be formed in a disk-like configuration having a diameter W and a thickness T disposed orthogonally with respect to the direction of the blood flow. In this case, like FIG. 1, an image of the vessel vertically sectioned in the direction of the blood stream will be captured in the "swing and tilt" photography. The diameter W is determined by the diameter of the blood vessel. The thickness T is determined by the beam width of the light application system. When the disklike cross section of the blood vessel is similar to a complete circle, the area of the cross section can be simply determined from the diameter W. When the cross section is deviated from a complete circle, the area of the cross section may be determined in the same manner as shown in FIG. 2.

Figure 4:
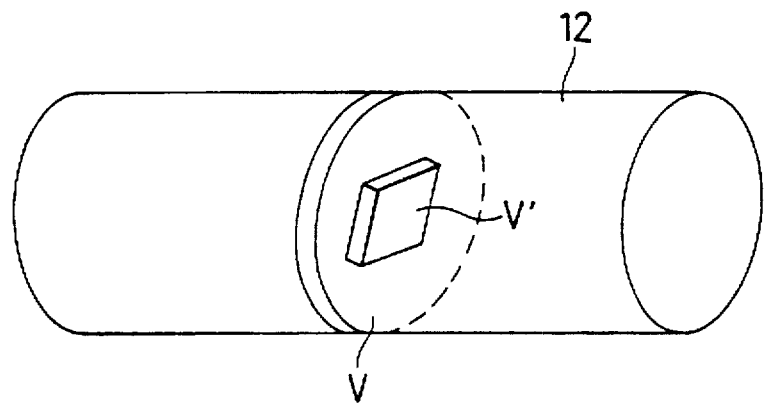
FIG. 4 is a view showing an example of a detection region according to the present invention.

In FIGS. 2 and 3, the entire region V might not be accommodated in the imaging screen. In other words, as shown in FIG. 4, only a region V' which constitutes part of the region V is displayed on the entire surface of the screen. In such case, the entire portion displayed on the screen can be regarded as a magnified image of the detection region V (V' is regarded as V).

In this manner, images of the dynamic state of the blood cells flowing through the blood vessels can be captured from the direction of the blood stream.

Referring to FIG. 1, the video system 44 provides a video tape recorder (VTR) for recording an image captured with the CCD 40. The recorded image is processed at the image processing circuit 46 and is sent to means 48 for calculating the number of red blood cells, means 50 for calculating MCV, means 52 for calculating HGB, means 54A for calculating HCT, means 54B for calculating MCH, means 54C for calculating MCHC, means 56A for calculating the number of white blood cells, means 56B for classifying white blood cells, and means 57 for calculating the flow rate of blood thereby analyzing the morphology (including the tone) and/or number of the blood cells to calculate each of the items of the blood test.

In addition, the image processing circuit 46 selectively provides the functions of each kind of filter, γ(gamma) correction, interpolation, jitter correction, tone conversion, color balance correction, white balance, and shading correction to perform pretreatment of images.

Figure 8:
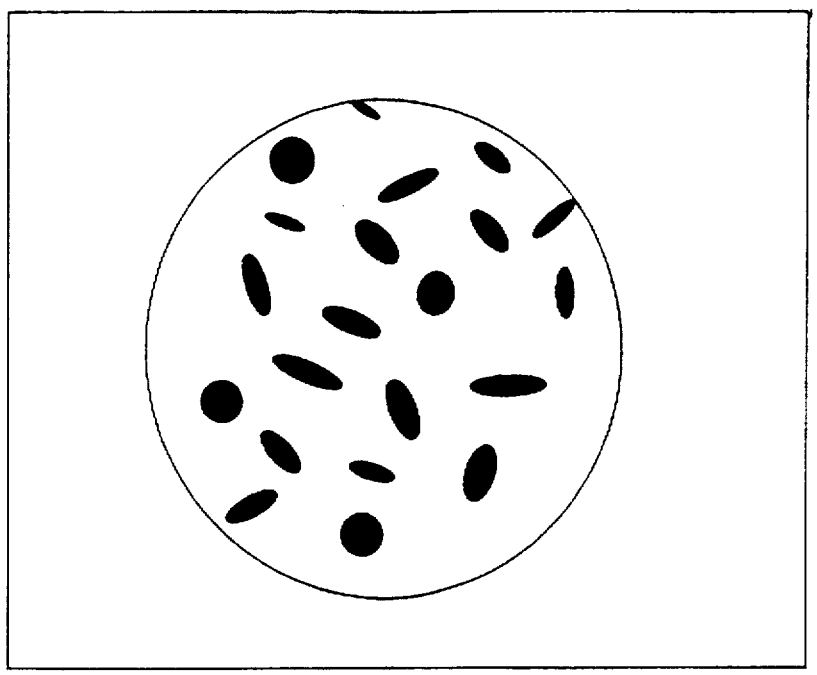
FIG. 8 is a view illustrating a captured image.
Figure 9:
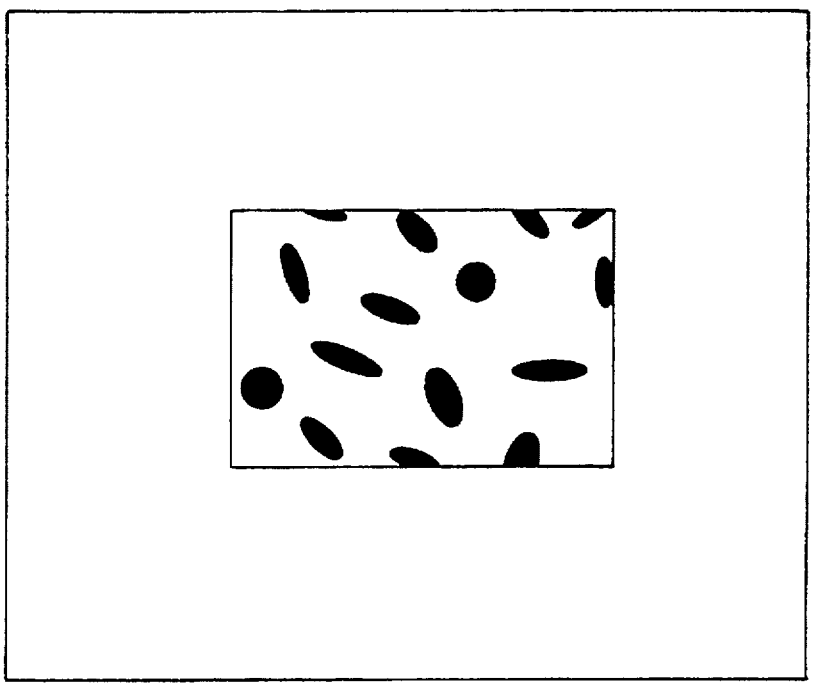
FIG. 9 is a view showing a state in which an image is cut out through a window.
Figure 10:
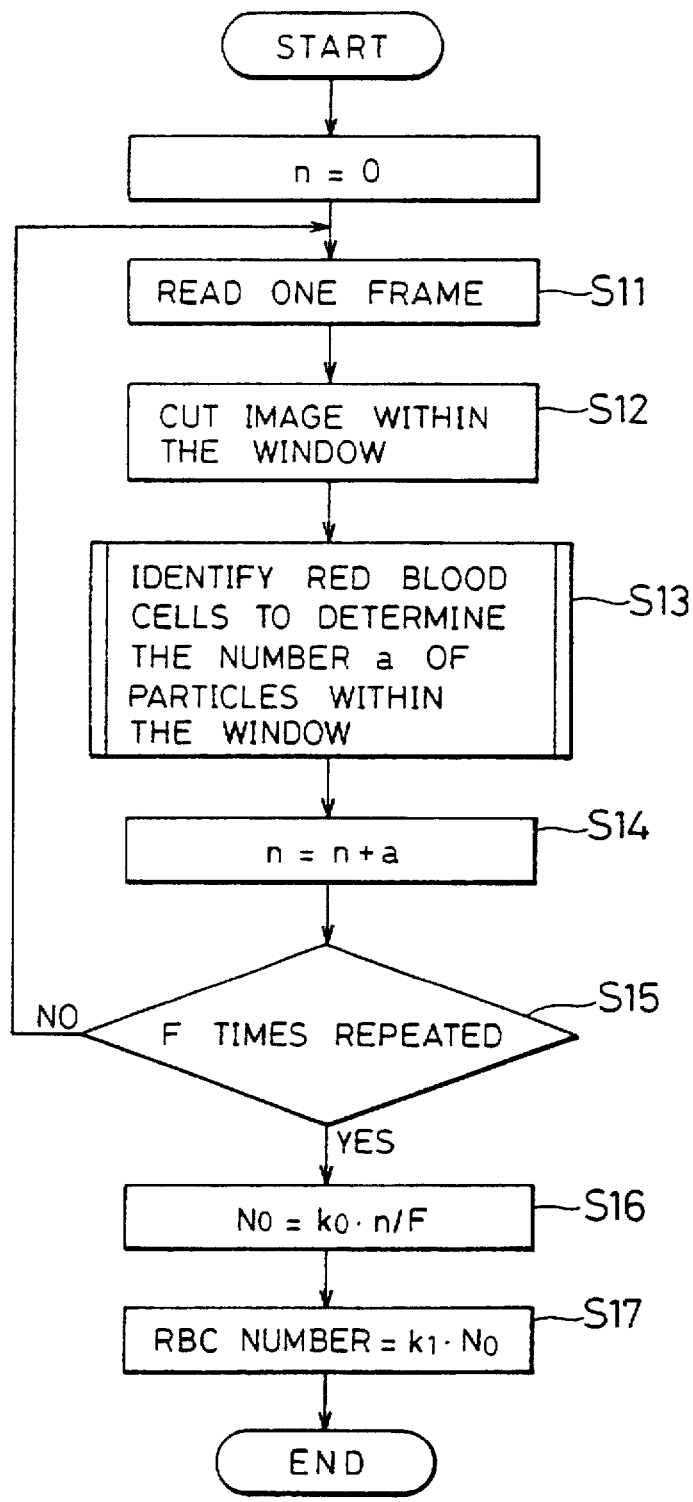
FIG. 10 is a flow chart showing a procedure for calculating the number of red blood cells (erythrocytes).

Subsequently, the means 48 for calculating the number of red blood cells will be detailed hereinafter. The means 48 for calculating the number of red blood cells calculates the number of red blood cells (RBC) per unit volume by counting the number of red blood cells in images of the region V. The procedure of the calculation is shown in the flowchart in FIG. 10. In FIG. 10, an image frame as shown in FIG. 8 of the region V is read one by one from the video system 44 (step 11), followed by cutting out the read image with a window having a predetermined size as shown in FIG. 9 (step S12), and identifying red blood cells in the window to determine the number a of red blood cells in the window (step S13).

This operation is repeated for a predetermined number F of frames to determine the sum n of the number a of red blood cells obtained in each operation (steps S14 and S15), thereby calculating the mean red blood cell per unit volume represented by $N_0 = k_0 \cdot n/F$ (step S16). In the formula, symbol $k_0$ is a conversion constant determined from the window size, the imaging magnification and the thickness T of the region V. When necessary, the obtained $N_0$ is multiplied by a correction constant $k_l$ to translate data on arteriolas and veinlets (capillary vessels) into the number of red blood cells (RBC) corresponding to the medium-size and large blood vessels (step S17).

Figure 11:
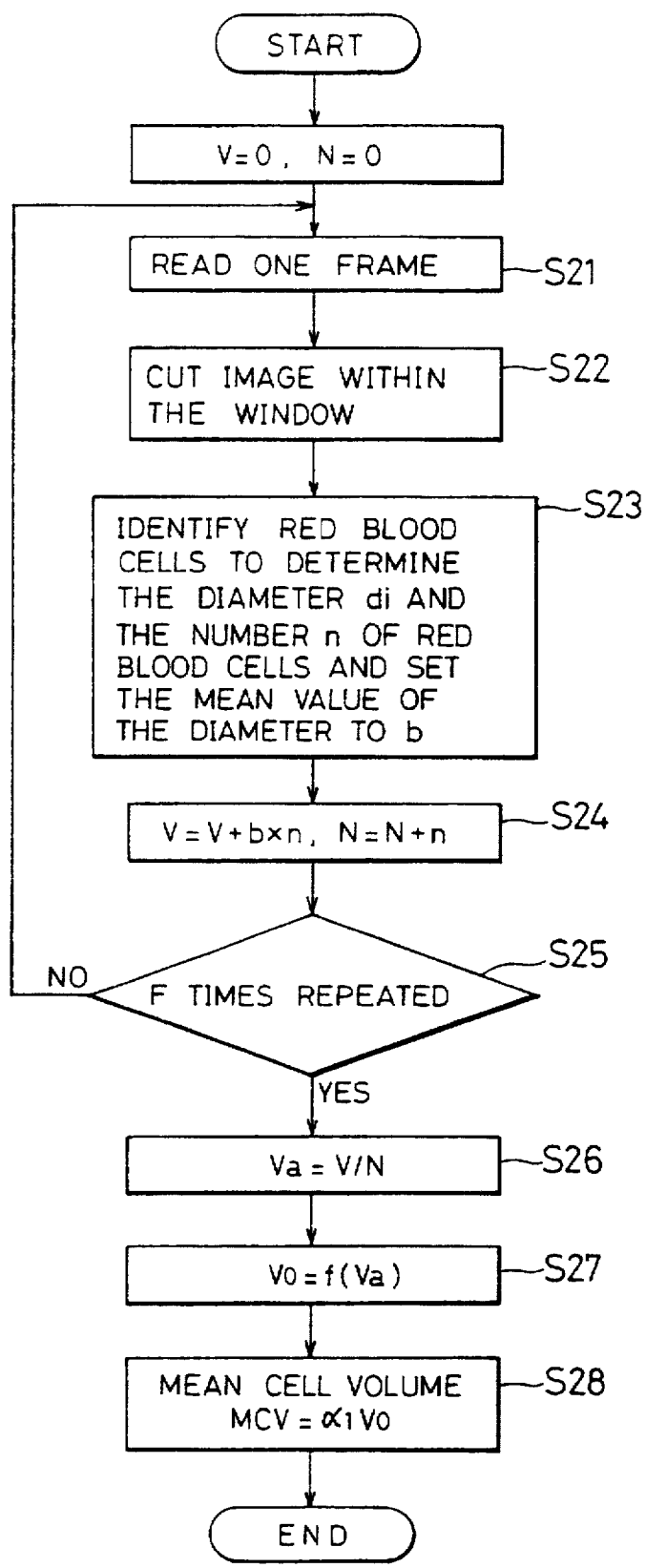
FIG. 11 is a flow chart showing a procedure for calculating MCV.

With respect to the image processing of red blood cells at step S23, a known method may be employed (for example, see "An Algorithm of Automated RBC Classification and Its Evaluation" by Akihide Hashizume et al, Medical Electronics and Bio-Engineering, Vol. 28, No. 1, March 1990). Alternatively, two continuous captured images in which red blood cells have moved by approximately 0.1 micron (showing a time lag of one hundred thousandth of a second at the blood stream of 10 mm per second) may be subjected to subtraction processing so that red blood cells can be identified at a higher speed from a two-dimensional differential image in which only edges of moving red blood cells are emphasized. Subsequently, the means 50 for calculating MCV will be explained hereinafter. The means 50 determines the mean corpuscular volume (MCV) by determining an area of each red blood cell from the image and multiplying the mean value of the area of each red blood cell by a predetermined constant to calculate the volume value. The procedure is shown in the flowchart in FIG. 11. In FIG. 11, a frame of an image is read by one by one from the video system 44 (step 21) followed by cutting the image thus read with a window having a predetermined size (step 22) and identifying red blood cells in the window to determine the diameter di and the number n of red blood cells, thereby calculating the mean value b of the diameter (step S23).

The same operation is repeated for a predetermined number of frames F to determine the sum V of the diameters b x n and the sum N of the numbers n obtained in each operation (steps S24 and S25). The sum V of the diameters is divided by the sum N of the numbers to calculate the mean diameter $V_a$ (step S26) to determine the volume $V_0$ by using a function f (experimentally determined function) for translating the diameter into the volume (step S27). Then the volume $V_0$ thus given is multiplied by a correction constant $\alpha_1$ to determine the mean corpuscular volume (MCV) corresponding to the medium-size and large arteries and veins from data on the arteriolas and veinlets as well as capillary vessels (step S28).

Then, means 52 for calculating the amount of hemoglobin will be explained hereinbelow. The means 52 calculates the total amount of hemoglobin (HGB) per unit area from the intensity of light incident to the region V and the intensity of light reflected at the region V in accordance with the following principle.

When the intensity of incident light is represented by $Io(\lambda)$ and the intensity of the reflection light by $I(\lambda)$, the following formula is established:

$$I(\lambda) = Io(\lambda) \cdot \alpha(\lambda) \times \exp((\epsilon_1(\lambda)HgbO_2 + \epsilon_2(\lambda)Hgb)) \quad (1)$$

where $\alpha(\lambda)$ represents a scattering term (which depends on the wavelength), $\epsilon 1(\lambda)$ an absorption constant of oxyhemoglobin (which depends on the wavelength), $\epsilon 2(\lambda)$ an absorption of deoxyhemoglobin (which depends on the wavelength), $HgbO_2$ a concentration of oxyhemoglobin, Hgb a concentration of deoxyhemoglobin and $\lambda$ a wavelength.

The total amount of hemoglobin HGB per unit volume is determined by the formula:

$$HGB = HBgO_2 + Hgb \quad (2)$$

The scattering term of formula (1) can be regarded approximately as a constant by appropriately selecting a predetermined wavelength $\lambda$. When the scattering term is represented by $\alpha_0$, the formula (1) can be represented as $$\log(I(\lambda)/Io(\lambda)) = (\epsilon_1(\lambda)HgbO_2 + \epsilon_2(\lambda)Hgb) + \log\alpha_0 \quad (3)$$

By the way, $I(\lambda)/Io(\lambda)$ is a value obtained in the measurement. Then $\epsilon_1(\lambda)$ and $\epsilon_2(\lambda)$ become constants with respect to the selected wavelength, and three values $HgbO_2$, Hgb, and $\alpha_0$ remain as unknown values.
Therefore, the following results are produced.

(a) Two values $HgbO_2$ and Hgb are determined by measuring $I(\lambda)/I_o(\lambda)$ with respect to appropriate three wavelengths.

(b) When $\alpha_0$ does not depend on living bodies and is assumed to be constant, two values $HgbO_2$ and Hgb can be determined by measuring the two values on condition that $\alpha_0$ is preliminarily determined in tests (there is no problem for practical purposes when $\alpha_0$ is assumed to be constant).

(c) Furthermore, selecting a wavelength (for example, 525 nm) at which the oxygen type and the deoxygen type Hgb have the same light absorbance produces a result of $\epsilon_1(\lambda) = \epsilon_2(\lambda)$. The total amount of hemoglobin per unit volume can be determined by the wavelength.

Incidentally, in the field of blood analysis, the total amount of hemoglobin is simply referred to as hemoglobin. Thus the amount will be described as such hereinbelow.

In accordance with the above principle, the means 52 for calculating hemoglobin calculates HGB. The calculation follows any of the three procedures shown in the flowchart in FIGS. 12 to 14.

Figure 12:
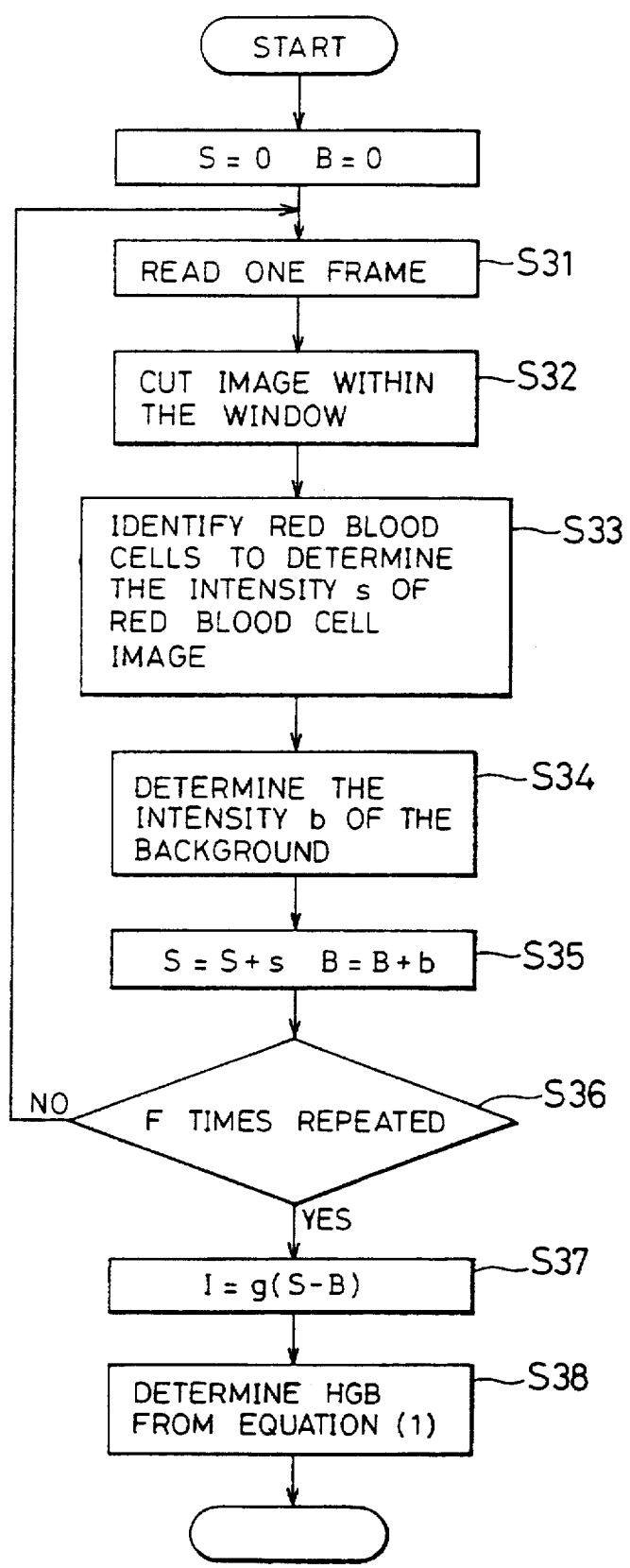
FIG. 12 is a flow chart showing a procedure for calculating hemoglobin.

At the outset, the procedure shown in FIG. 12 is characterized by determining the intensity $I(\lambda)$ of reflected light from the sum of the intensity of images. In other words, each image frame is read from the video system 44 (step S31), cutting out the read image with a window having a predetermined size and recognizing red blood cells within the window to determine the intensity s of the red blood cell image. Then, the intensity b at the background of the image is determined (step S34).

Each of the sums S and B of the thus obtained intensities s and b is determined by repeating the above operations for the predetermined number F of frames (steps S35 and S36). Then the intensity $I(\lambda)$ is calculated by the function g with which the intensity $I(\lambda)$ is determined from a difference between S and B (step S37). Incidentally, function g was experimentally determined. Then the hemoglobin and HGB are determined by the formula (1) on condition that $Io(\lambda)$ is already known (step S38).

Figure 13:
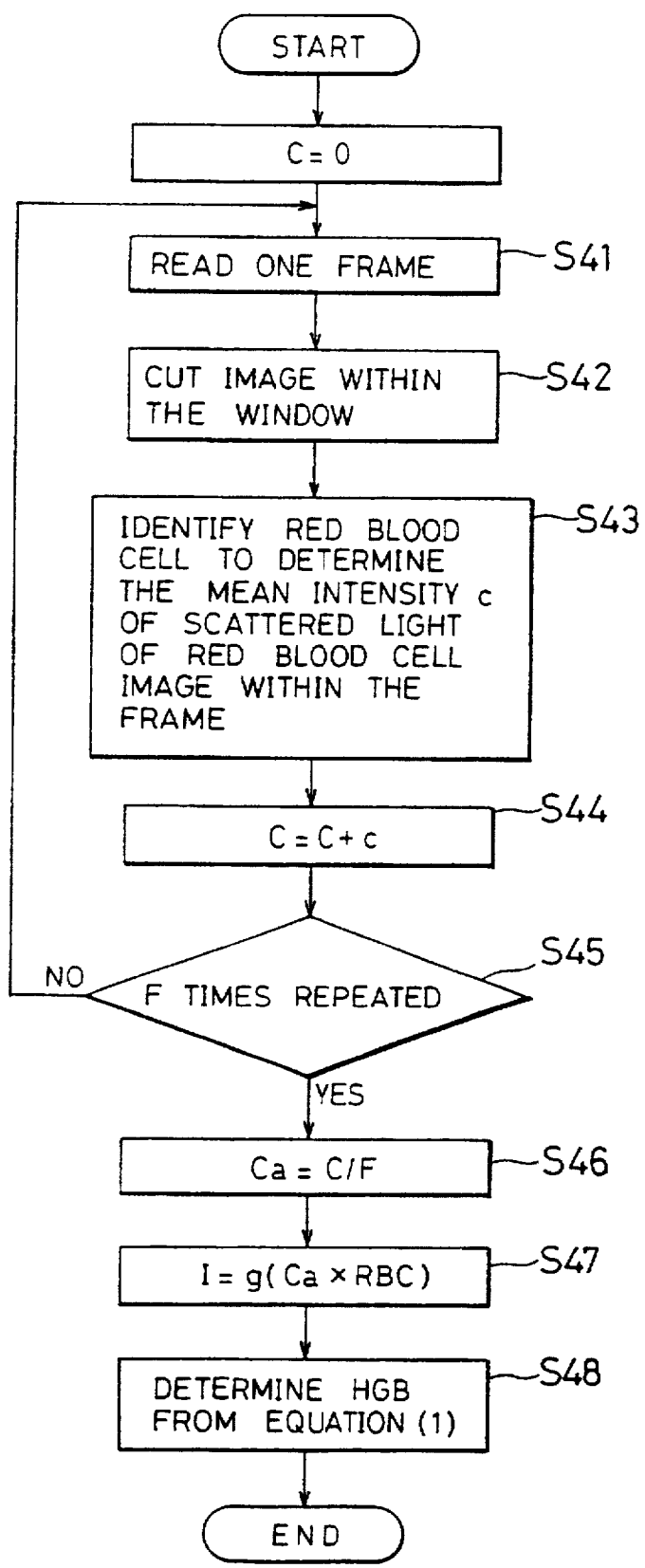
FIG. 13 is a flow chart showing a procedure for calculating hemoglobin.

Then, the procedure shown in FIG. 13 is characterized by determining the intensity $I(\lambda)$ of the reflected light from the mean concentration of red blood cells. In FIG. 13, each image frame is read from the video system 44 (step S41) followed by cutting out the read image with a window having a predetermined dimension (step S42), identifying red blood cells within the window, and determining the mean scattered light intensity (step S43).

The sum C of the intensity c is determined which is obtained in each operation by repeating the above operation for the predetermined number F of frames (step S44 and S45) followed by calculating the mean scattered light intensity Ca with respect to one red blood cell (step S46). Then $I(\lambda)$ is determined by using a function (experimentally determined) in which $I(\lambda)$ is determined from the mean intensity Ca and the red blood cell number (RBC) (step S47). Given that $Io(\lambda)$ is already known, hemoglobin (HGB) is determined from the formula (1) (step S48).

Incidentally, one of the above procedures (shown in FIG. 12 and FIG. 13) which has a smaller difference between frames can be adopted by executing either the procedure shown in FIG. 12 or the procedure shown in FIG. 13. When the light source 22 applies light having two wavelengths, either the procedure shown in FIG. 12 or the procedure shown in FIG. 13 is executed with respect to each wavelength to determine the hemoglobin based on formula (1). In such a case, oxygen hemoglobin and the deoxygen hemoglobin can be respectively determined.

Figure 14:
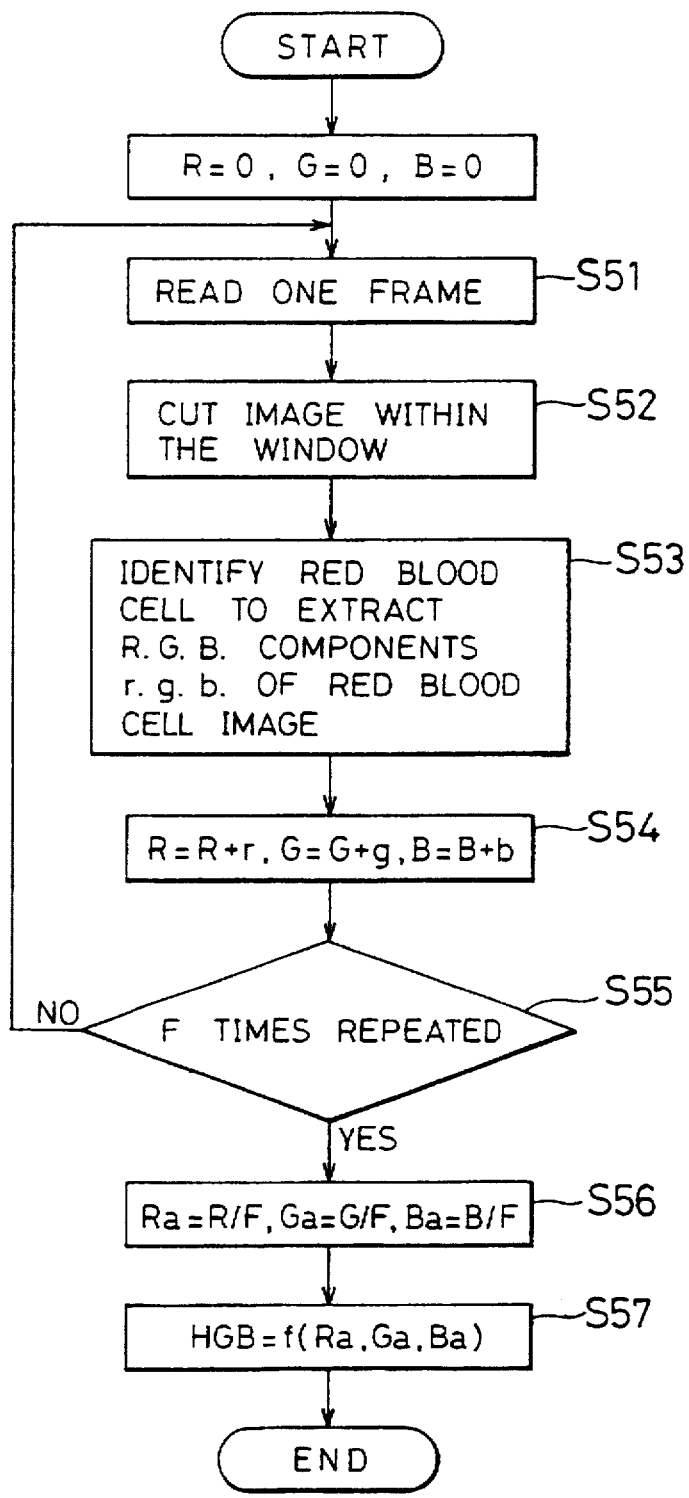
FIG. 14 is a flow chart showing a procedure for calculating hemoglobin.

Subsequently, the procedure shown in FIG. 14 is characterized by determining the hemoglobin from the tone of the image when light is applied which has three wavelengths, a white color, or a wide band spectrum. In FIG. 14, each image frame is read from the video system 44, the read image is cut out with a window having a predetermined size, and red blood cells in the window are identified while each component r, g, and b of R (red), G (green), and B (blue) colors in the red blood cell image is extracted (steps S51, S52 and S53).

The above operation is repeated for a predetermined number F of frames to calculate the respective sum R, G, and B of component r, g, and b obtained in each operation (steps S54 and S55). Then the mean original color components Ra, Ga, and Ba are determined (step S56) to calculate hemoglobin HGB by using a function experimentally determined in advance (step S57).

Subsequently, the means 54A for calculating a hematocrit value will be detailed hereinafter. The means 54A calculates the following equation to determine the hematocrit value HCT.

$$HCT = \alpha_2 \times (MCV) \times (RBC) \quad (4)$$

Here, MCV is a value determined by the means 50 for calculating MCV whereas RBC is a value determined by the means 48 for calculating the number of red blood cells. Then a2 is a correction constant for translating a value corresponding to veinlets into a value corresponding to medium-size to large arteries and veins.

Then, the means 54B for calculating the mean corpuscular hemoglobin (MCH) will be explained hereinbelow. The means 54B calculates the following equation to determine the mean corpuscular hemoglobin (MCH).

$$MCH = (HGB)/(RBC) \quad (5)$$

where HGB is a value determined by the means 52 for calculating the hemoglobin, and RBC is a value determined by the means 48 for calculating the number of red blood cells. Next, the means 54C for calculating the mean corpuscular hemoglobin concentration (MCHC) will now be explained. The means 54C calculates the following equation to determine the mean corpuscular hemoglobin concentration (MCHC).

$$MCHC = (HGB)/(HCT) \quad (6)$$

where HGB is a value determined by the means 52 for calculating the hemoglobin, and HCT is a value determined by the means 54A for calculating the hematocrit value.

Then, the means 56A for calculating the number of white blood cells will be explained hereinbelow. The means 56A calculates the number of white blood cells per unit volume by recognizing white blood cells in images of the region V and counting the number thereof. Since the procedure for calculating the number thereof is the same as the counterpart for calculating the number of red blood cells (RBC) as shown in FIG. 10, detailed description thereof is omitted here. The number F of frames has to be increased in the case of counting the white blood cells because the number of white blood cells is smaller than that of red blood cells (about one thousandth).

Figure 15:
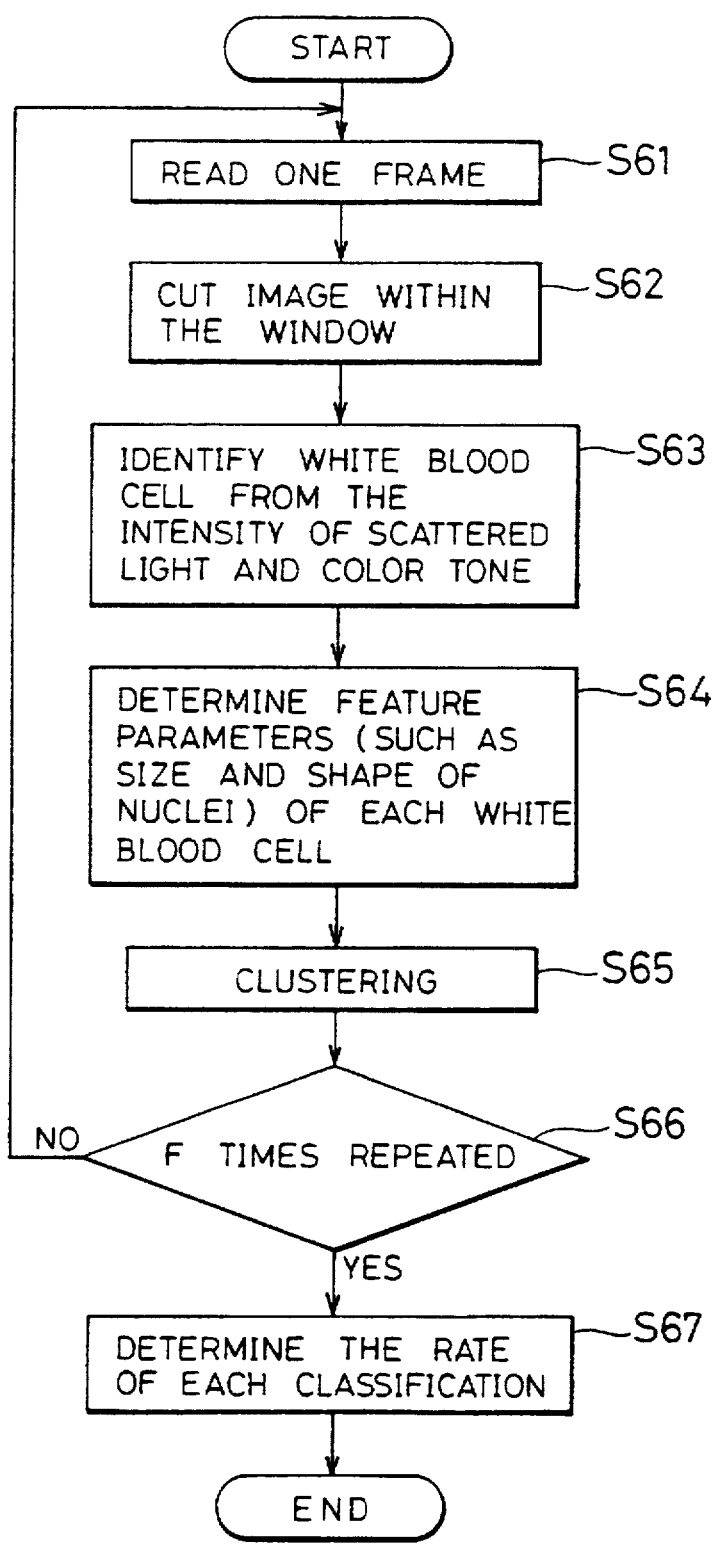
FIG. 15 is flow chart showing a procedure for classifying white blood cells (leukocytes).
Figure 16A:
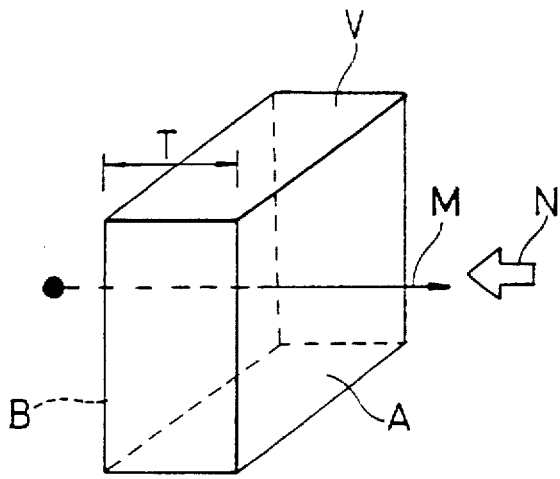
FIGS. 16(a) to 16(d) are views illustrating a principle of calculating the flow rate of blood.
Figure 16B:
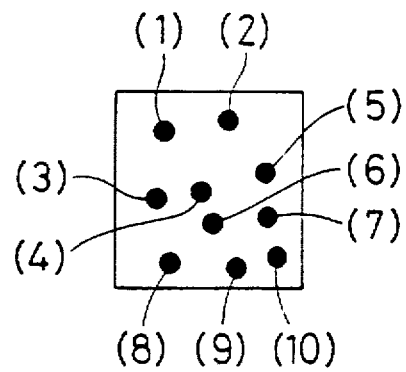
Figure 16C:
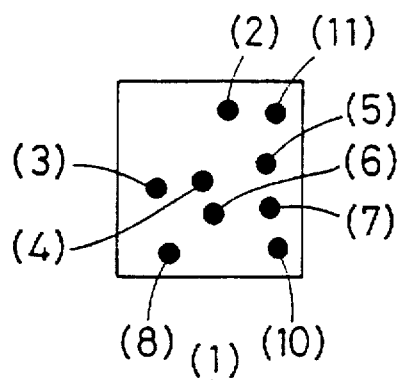
Figure 16D:
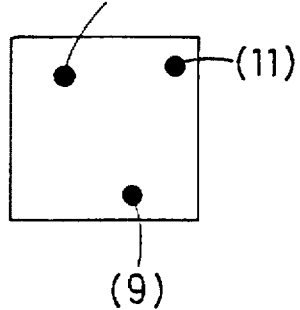

Next, the means 56B for classifying white blood cells will now be described. The means 56B classifies white blood cells into lymphocytes, monocytes, neutrophils, eosinophils, and basophils from morphological features. The procedure thereof is shown in the flowchart of FIG. 15. In FIG. 15, an image frame is read from the video system 44 (step S61), the read image is cut out with a window having a predetermined size (step S62), and white blood cells in the window are recognized from the intensity of scattered light and color tone (step S63).

Then the feature parameters (such as size, shape, size of nuclei, and shape of nuclei) of individual white blood cells are determined (step S64), and the classification is made in accordance with the determined feature parameters (step S65). The above operation is repeated for the predetermined number F of frames to calculate each classification ratio (step S67).

Then means 57 for calculating the rate of blood stream will be detailed hereinbelow. The means 57 can, as shown in FIGS. 2 and 3, provide a cross-section image of blood vessels, thereby enabling the calculation of the rate of blood stream with the principle shown in FIG. 16 (zero-cross method extended into space). In other words, when the particles pass through the detection region partitioned with parallel planar surfaces A and B spaced by T in the direction M as shown in FIG. 16 (a), the traveling particles are observed from the direction N.

Referring to FIG. 16 (b), ten particles are observed at time t. After time $\Delta t$, particles (1) and (9) located near the surface A get out of the region V. Also, a particle (11) located in the neighborhood of the surface B enters the region V. The particles that appear and disappear during the time $\Delta t$ with respect to the region V become apparent as shown in FIG. 16 (d) based on a difference between FIGS. 16 (b) and 16 (c). Then, assuming that the distribution density of the particles is constant, the frequency of appearance is proportional to the speed of the particles. In other words, when the speed is high, the frequency is high. When the speed is low, the frequency is low.

Suppose that the observed mean number of particles is represented by Na, and the mean number of particles that appear in the difference of the images observed at time t and t+$\Delta t$ is represented by Aa, particles go out of the region by Aa/2 during the time $\Delta t$. Time required for all the number Na of particles to move by distance T is $2\Delta t \cdot Na/Aa$. The average speed Xa of the particles is given by $$Xa = T \cdot Aa/(2\Delta T \cdot Na) \quad (7)$$

where $\Delta t$ is a predetermined value, and T is a known value. The means 57 uses this principle to allow the determination of Na and Aa with respect to red blood cells in the captured images by reading the images from the video system 44 so as to calculate the rate of blood stream from the equation (7).

Any information on each kind of blood cell (calculated value) can be translated into blood information that has been clinically used for the medium and large arteries and veins through multiplying the results with an experimentally determined correction constant.

Embodiment 2

Figure 5:
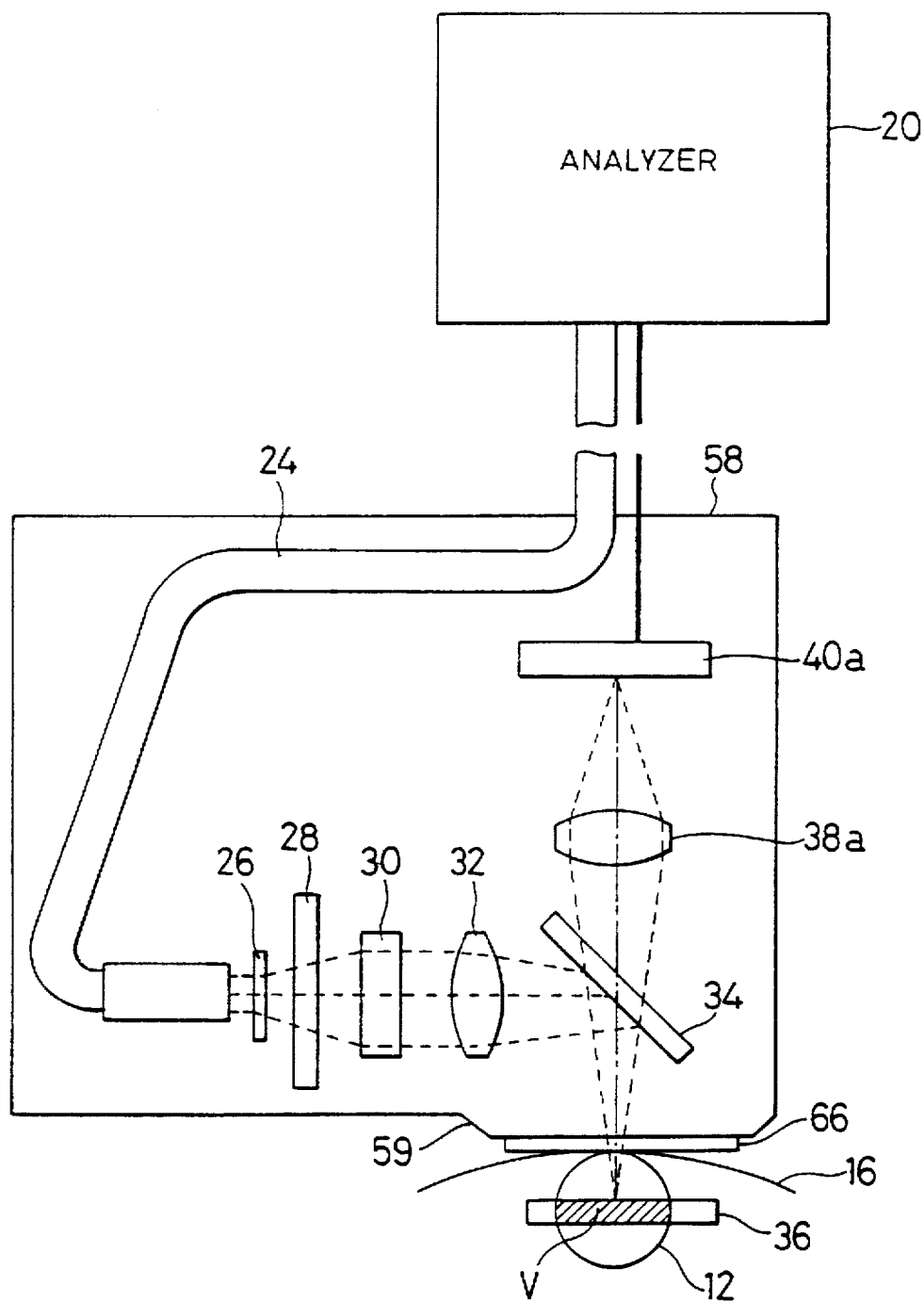
FIG. 5 is a view illustrating the structure of embodiment 2 of the present invention, the view showing an essential portion thereof.
Figure 6:
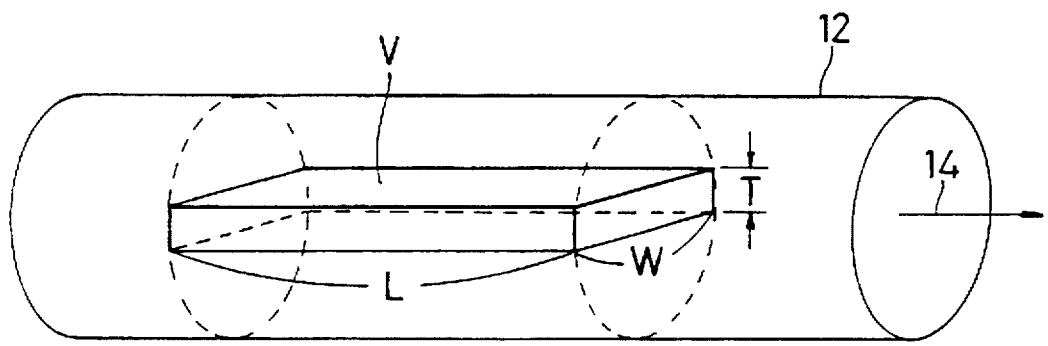
FIG. 6 is a view showing an example of a detection region according to the present invention.

FIG. 5 is a view showing a structure of embodiment 2 of the invention, the view showing an essential portion of the embodiment 2. FIG. 6 shows a case in which the light application device forms a thin belt-like detection region V having a width of W, a length of L and a thickness of T in parallel to the direction 14 of the blood stream through the vessel 12 thereby counting the number of blood cells that are present in the region V. Also in FIG. 5, a portion below the skin surface 16 is magnified for simplicity. Referring to FIG. 5, the direction of the blood stream is perpendicular to the paper surface. The main body 20 of the analyzer is the same as FIG. 1, so the drawings thereof is omitted here.

The light emitted from the light source 22 in the main body 20 of the analyzer irradiates the diffuser 26 via an optical fiber 24. Light is diffused by the diffuser 26 to uniformly irradiate a plate 28. The plate 28 substantially forms a surface light generator so that a real image of the plate 28 is formed across the blood vessel 12 via an optical system comprising a lens 30, a lens 32, and a dichroic mirror 34. Incidentally, an optical diffusion plate such as a frost type diffusion plate manufactured by Sigma Optical Materials Co., Ltd. is used as the plate 28.

The real image 36 of the plate 28 has a thickness of T. A region where the real image 36 of the plate 28 intersects the blood vessel 12 forms the detection region V.

Preferably, the optical path of irradiation at least from the skin surface 16 to the real image 36 is sharply narrowed down to obtain a good contrast between the brightness of the real image 36 and the brightness of other portions.

The width W of the region V is identical to the diameter of the blood vessel in FIGS. 5 and 6. The region V shown in FIG. 5 has a length of L in the direction of the paper surface (see FIG. 6). The length L is determined by the degree of aperture of the light application system.

The CCD 40a receives the light reflected at the region V via a dichroic mirror 34 and a lens 38a. Analyzing an image captured with the CCD 40a enables the determination of values for each item of hematology test from the morphology and/or the number of blood cells within images of the region V in the same manner as in FIGS. 1 and 2.

Figure 7:
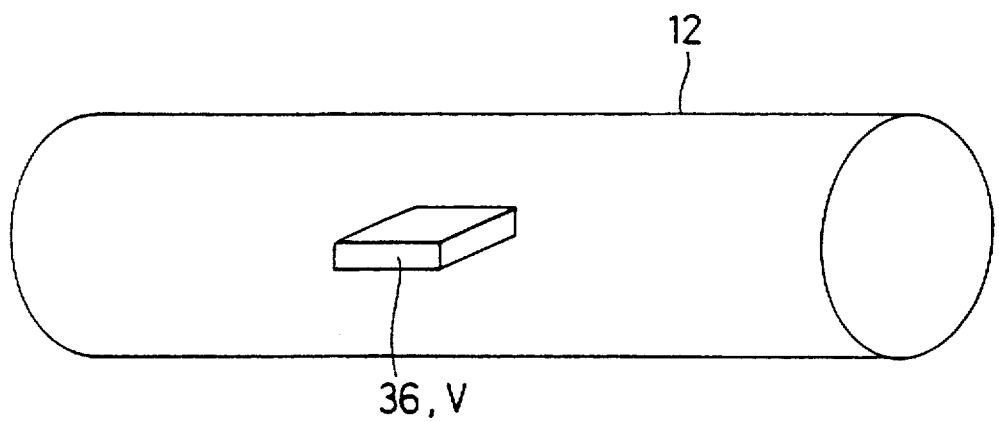
FIG. 7 is a view showing an example of a detection region according to the present invention.

Incidentally, FIGS. 5 and 6 show a case in which the real image 36 of the plate and the blood vessel 12 intersect each other. When the diameter of the blood vessel is large, the real image 36 of the plate 28 may be formed completely inside the blood vessel 12 as shown in FIG. 7. In such a case, the real image 36 of the plate itself constitutes the detection region V.

In addition, both in FIGS. 6 and 7, the magnification might be too large to allow the whole volume of the region V for detection to be accommodated within the imaging screen. In such a case, the whole screen may be regarded as a magnified image of the detection region V. The actual size of the width W and the length L of the region W are determined through dividing the horizontal width and vertical width of the screen by the magnification of the image capturing system. The thickness T of the region W is identical to the thickness of the real image 36 of the plate 28.

Incidentally, in embodiment shown in FIG. 5, the detection region V is generated by forming the real image 36 of the plate 28 inside of living bodies. A region V similar to the one shown in FIG. 5 can be formed by applying a laser light to living bodies from different directions via a conversion lens and a scanning device to form a focus (common focus) at a certain depth in living bodies.

In any case, since light is applied to a region having a certain depth in living bodies, there will be an extremely small effect of scattered light from other portions of living bodies, for example, portions deeper than a position where blood vessels to be measured are located.

Embodiment 3

Figure 18:
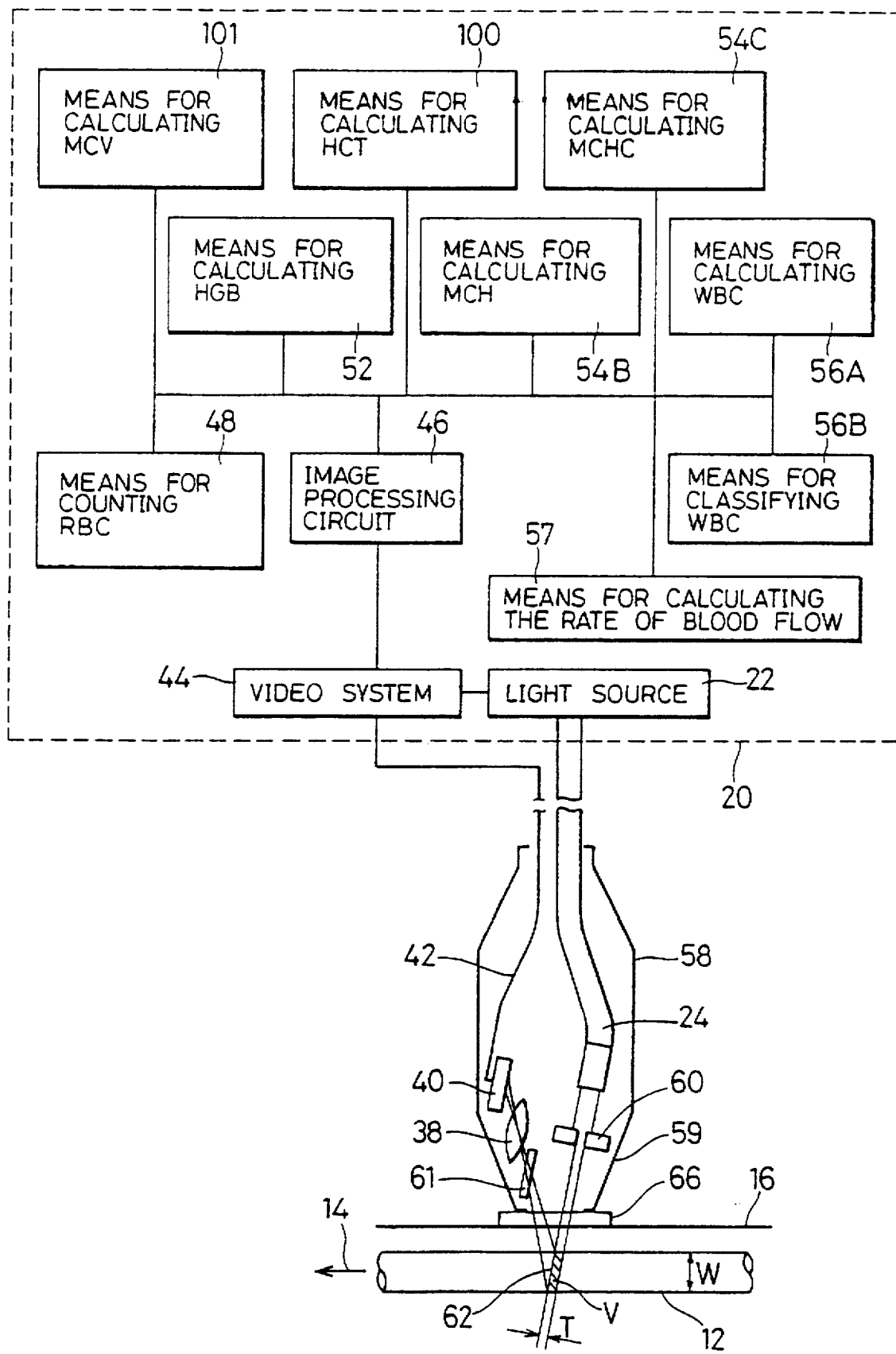
FIG. 18 is a view showing a construction of embodiment 3 of the present invention.

FIG. 18 is a view showing a structure of embodiment 3 of the present invention. The structure shown in FIG. 18 is formed such that the hematocrit value calculating means 54A and the mean corpuscular volume calculating means 50 in the structure shown in FIG. 1 is replaced by means 100 for calculating hematocrit value and means 101 for calculating the mean corpuscular volume. Other portions are the same as in the structure shown in FIG. 1.

The means 100 for calculating the hematocrit value in this embodiment will be explained.

The means 100 for calculating the hematocrit value calculates a hematocrit value (HCT) from a ratio of the area occupied by the image of red blood cells to a predetermined area of the image captured by the video system 44 and processed by the image processing circuit 46. The procedure for the calculation of the value is shown in the flowchart of FIG. 19.

Figure 19:
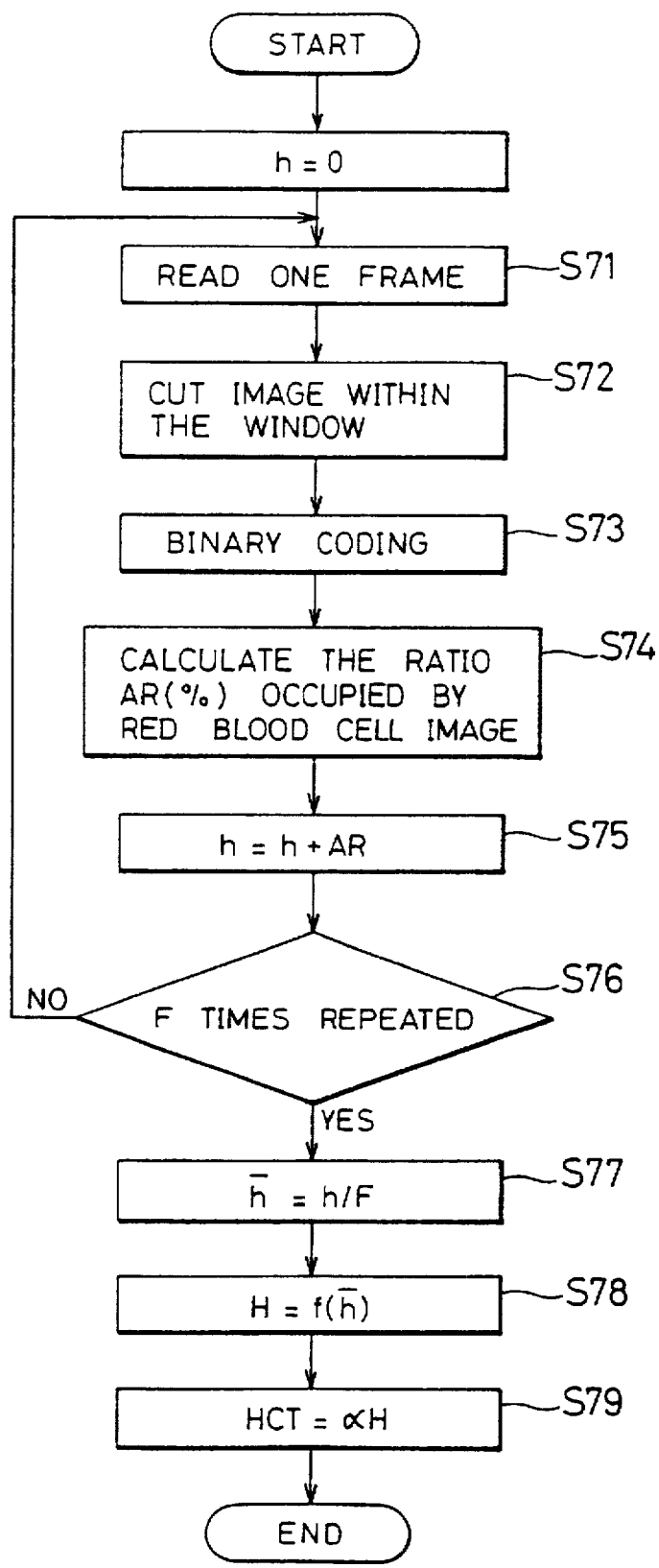
FIG. 19 is a flow chart showing a procedure of calculating hematocrit value of the embodiment shown in FIG. 18.

In FIG. 19, the procedure involves reading a frame of an image as shown in FIG. 8 of the region V one by one from the video system 44 (step S71), cutting the read image with a window having a predetermined size (step S72), thresholding the image of the red blood cells within the window with an appropriate value (step S73), and determining the ratio AR (%) of the area occupied by the red blood cell image to the area of the window (step S74).

This operation is repeated for the predetermined number F of frames (step S76) to determine the cumulative sum h of AR which is provided in each operation (step S75), thereby calculating the mean value by dividing h by F (step S77), and determining H by using a function g (which has been theoretically and experimentally determined) for correcting the overlap of the red blood cells (step S78). The H thus given is multiplied by a correction constant a to determine a hematocrit value HCT corresponding to the medium and large size arteries and veins out of data on arteriolas and veinlets (step S79).

Then, the means 101 for calculating the mean corpuscular volume will be explained hereinafter. The means 101 operates the following equation to determine the mean corpuscular volume (MCV).

$$MCV = (HCT)/(RBC) \tag{8}$$

where HCT represents a value determined by the hematocrit value calculating means 100, and RBC represents a value determined by the means 48 for calculating the number of the red blood cells.

The means 54A for calculating the hematocrit value as shown in FIG. 1 calculates the hematocrit value (HCT) from the mean corpuscular volume (MCV) and the number of red blood cells. In this case, the calculation time is relatively long because each erythrocyte is recognized and the configuration thereof has to be analyzed in order to determine MCV.

However, the hematocrit value calculation means 100 in the embodiment shown in FIG. 18 is not required to recognize each erythrocyte and can obtain HCT directly from images. Thus the calculation time is extremely shortened. Besides, when the calculation time is shortened, the analysis of various screens can be made possible with the result that the accuracy in the calculation of HCT is improved.

Embodiment 4

Figure 20:
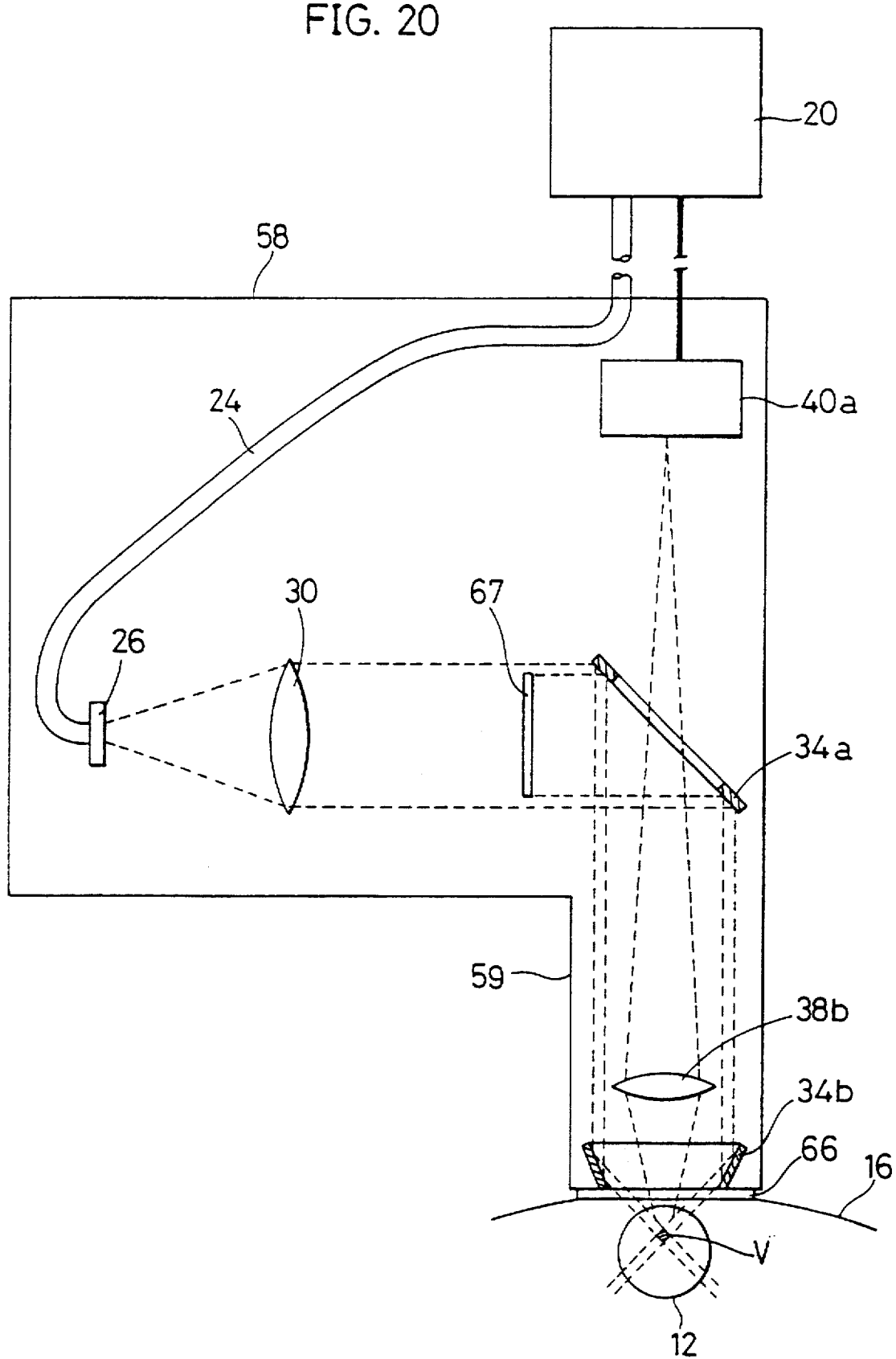
FIG. 20 is a view showing a structure of embodiment 4 of the present invention.

FIG. 20 is a view showing a structure of embodiment 4 of the present invention. Like numerals designate like elements in FIG. 1. Referring to FIG. 20, light generated by the light source in the main body 20 of the analyzer is led into the probe 58 through the optical fiber 24 to irradiate the diffuser 26. Light is diffused by the diffuser 26 and converted into parallel light by the collimator lens 30. The central portion of the collimated light is shielded by a disk-like shield 67, whereas the periphery of the collimated light is directed to the outside from the tip 59 of the probe 58 via ring-like mirrors 34a and 34b. Light directed to the outside from the tip 59 of the probe 58 irradiates the detection region V in the blood vessel 12 via the transparent plate 66 and the skin surface 16. The light reflected from the detection region V is received by the CCD 40a via the transparent plate 66 and an object lens 38b. The main body 20 of the analyzer analyzes an image captured by the CCD 40a. The analyzer 20 analyzes the captured images of the detection region so as to calculate blood components (for example, intensity of the transmitted or reflected light is determined from the images, so as to analyze hemoglobin).

The non-invasive blood analyzer according to this embodiment is characterized by irradiating the detection region with a dark-field illumination so as to improve the contrast of an image that is captured.

Figure 23:
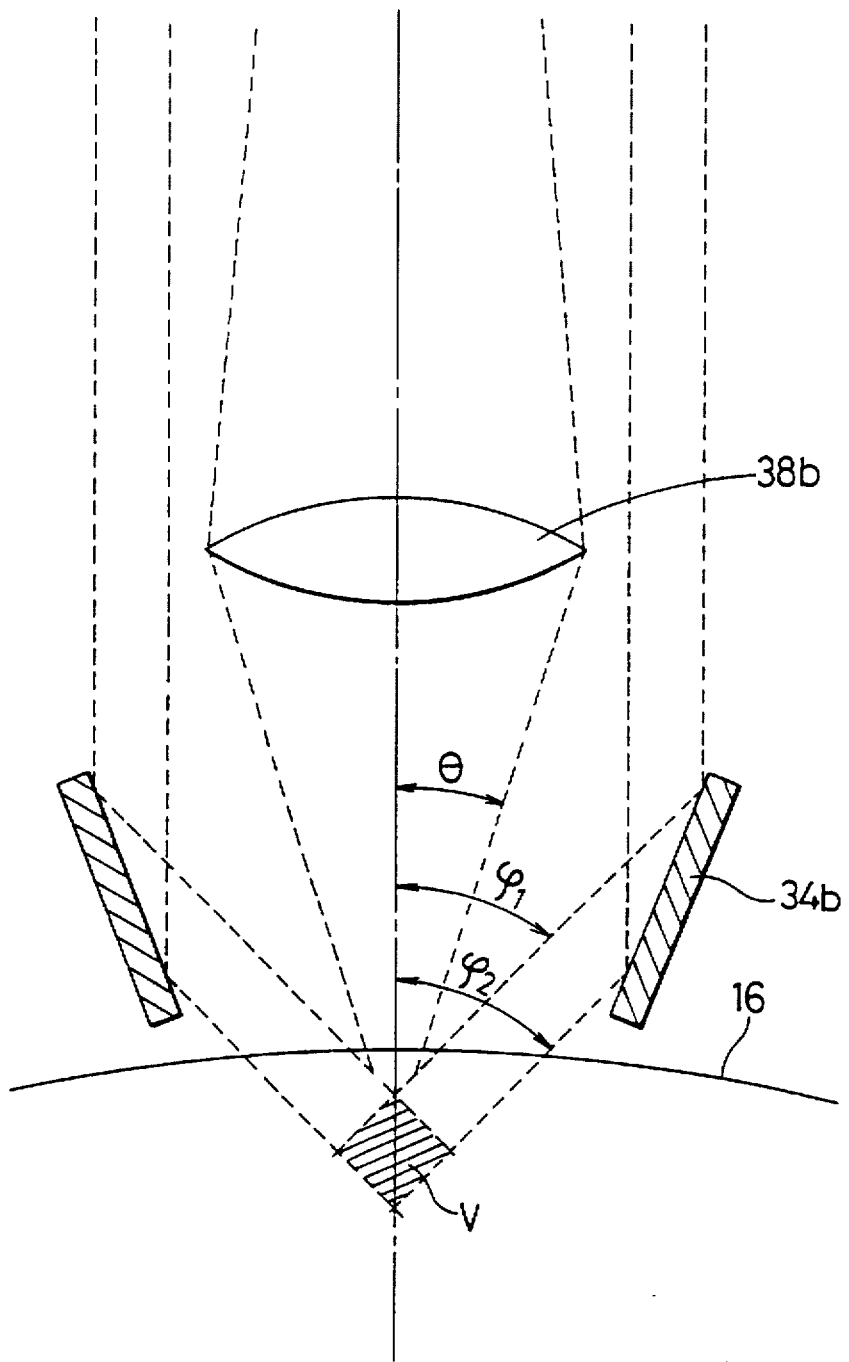
FIG. 23, is a partial expanded view of FIG. 20.

The dark-field illumination defined here refers to an illumination mode by which the illumination light is directed to the detection region V from the outside of the object lens 38b, as shown in FIG. 23. In other words, the illumination light illuminates the detection region V at an incident angle Φ1 or Φ2 larger than an aperture angle θ of the object lens 38b with respect to the detection region V.

Consequently, since the illumination light reflected at the skin surface 16 is directed to the outside of the aperture angle θ of the object lens 38b, thus failing to reach the CCD 40a, the contrast of the image captured by the CCD 40a is greatly improved. Here, each blood component has respective absorption characteristics. In order to obtain images for blood component A, a light is employed having a wavelength for which the blood component A shows a large absorptivity, so as to capture images of A with a good contrast.

FIG. 21 is a view showing a state in which the probe 58 shown in FIG. 20 and part of the subject (finger nail wall) are relatively fixed. An L-shaped support base 71 is attached to the probe 58. The tip 59 of the probe 58 provides a cylinder 59a extending from the probe 58, and a sliding cylinder 59b attached on the external circumference of the end of the cylinder 59a. The sliding cylinder 59b can slide in the directions of arrows a and b. The transparent plate 66 is fixed to the end of the sliding cylinder 59b.

Springs 72a, 72b are provided on the end of the cylinder 59a that urge the sliding cylinder 59b in the direction of the arrow b. An internal cylinder 73a incorporates the object lens 38b and the ring-like mirror 34b and is fixed to the probe 58 via a micro-motion element 74. Here, the support base 71, the cylinder 59a, the sliding cylinder 59b, the springs 72a, 72b, and the transparent plate 66 constitute fixing means, while the sliding cylinder 59b, the springs 72a, 72b, and the transparent plate 66 also constitute stabilizing device.

When a finger 75 of the subject is inserted between the support base 71 and the transparent plate 66 as shown in FIG. 21, the springs 72a, 72b press the transparent plate 66 on the nail wall of the finger 75 at an appropriate pressure. The detection region V in the blood vessel of the nail wall is fixed in the sight of the CCD 40a, thereby preventing a shift motion of the detection region V caused by the fine vibration of the finger 75.

In addition, the focus of the CCD 40a is adjusted by moving the lens 38b in the direction of the optical axis (in the direction shown by arrow a or b) with the micro-motion element 74. As the micro-motion element 74, for example, an element with a piezo element P-720/P-721 (manufactured by Physik Instrumente), or an element with an ultrasonic motor may be used.

The transparent plate 66 is detachably attached on the tip 59 of the probe 58 so that the plate 66 can be replaced for each subject. The transparent plate 66 can be replaced for hygienic reasons, i.e., for protecting subjects from contracting diseases.

A glass plate, a resin-made flexible film, or the like may be used as the transparent plate 66.

Alternatively, the transparent plate 66 itself may not be replaced, and a replaceable film may be closely contacted to the finger 75.

Figure 22:
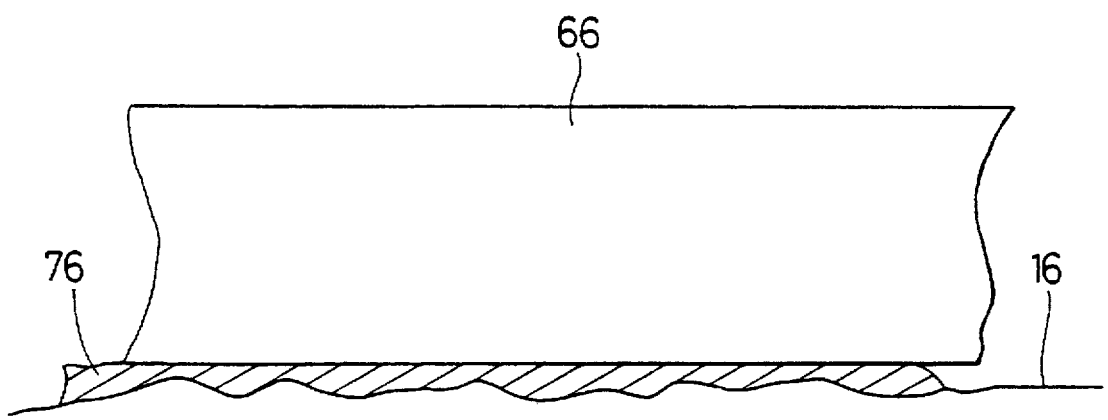
FIG. 22 is a view illustrating an essential part of FIG. 21.

Furthermore, as shown in FIG. 22, a liquid or gelatinous optical medium 76 which is safe for the living body is more preferably intervened between the skin surface 16 and the transparent plate 66 in order to prevent the illumination light from irregularly reflecting on the skin surface 16 and to obtain a sharp image of the detection region V.

As the light medium 76, oil or cream may be used. In embodiment 4, a transparent plate is used as the plate 66 contacting the living body. Instead of plate 66, however, an opaque plate with a light transmitting hole at a central portion thereof may be used, since the opaque plate can prevent the shift of the detection region.

Embodiment 5

Figure 24:
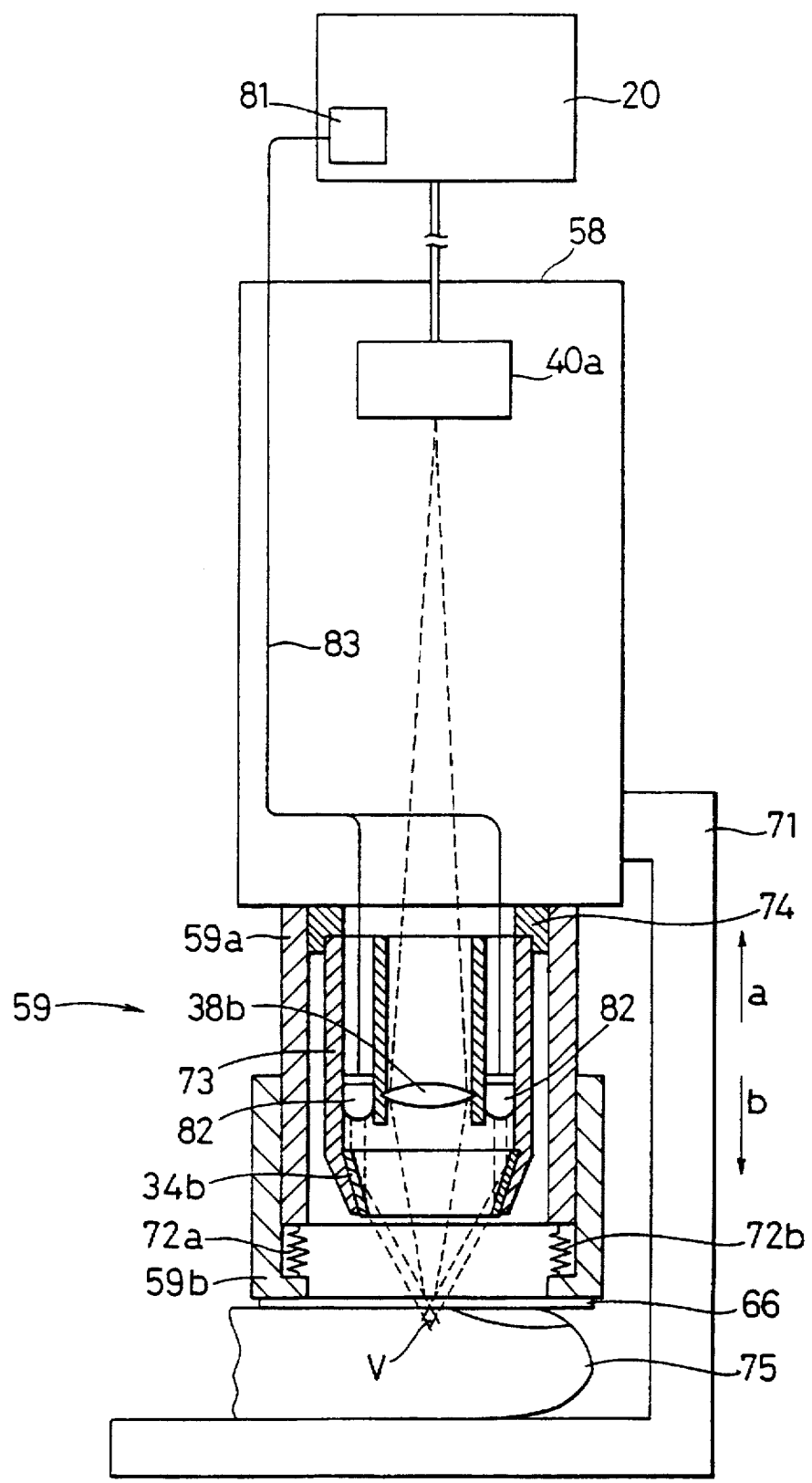
FIG. 24 is a view showing a structure of embodiment 5 of the present invention.

FIG. 24 is a view showing a structure of embodiment 5 of the present invention. Embodiment 5 is a partial modification of an apparatus shown in FIG. 21 and is equivalent to the apparatus of FIG. 21 except that a power circuit 81, a LED 82, and a connection cable 83 are provided instead of the light source 22, the optical fiber 24, the diffuser 26, the collimator lens 30, the disk-like shield 67, and the ring-like mirror 34a disposed in the main body 20 of the analyzer and in the probe 58 of the apparatus shown in FIG. 21. Elements identical to those in FIG. 21 are represented by the same numerals and the explanation thereof is omitted.

Figure 25:
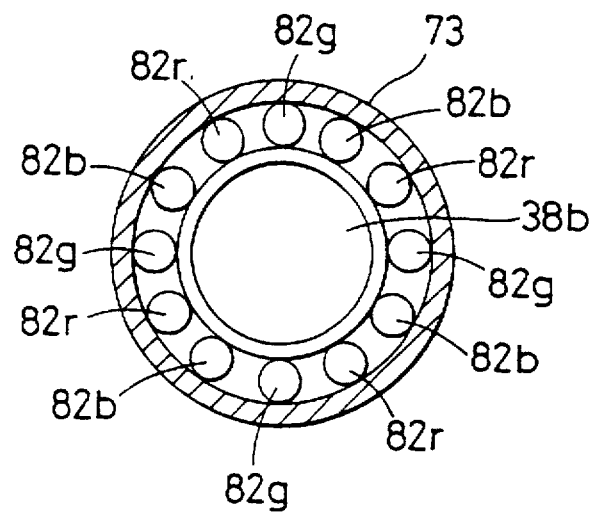
FIG. 25 is a view showing a cross section of an essential part of embodiment 5 of the present invention.

FIG. 25 is a view showing a cross section of an essential part of the apparatus shown in FIG. 24 as seen from the tip 59 of the probe 58. Four green LEDs 82g (with peak wavelength at 560 nm), four blue LEDs 82b (with peak wavelength at 450 nm), and four red LEDs 82r (with peak wavelength at 660 nm) are disposed as LED 82 circularly around the lens 38b.

Figure 26:
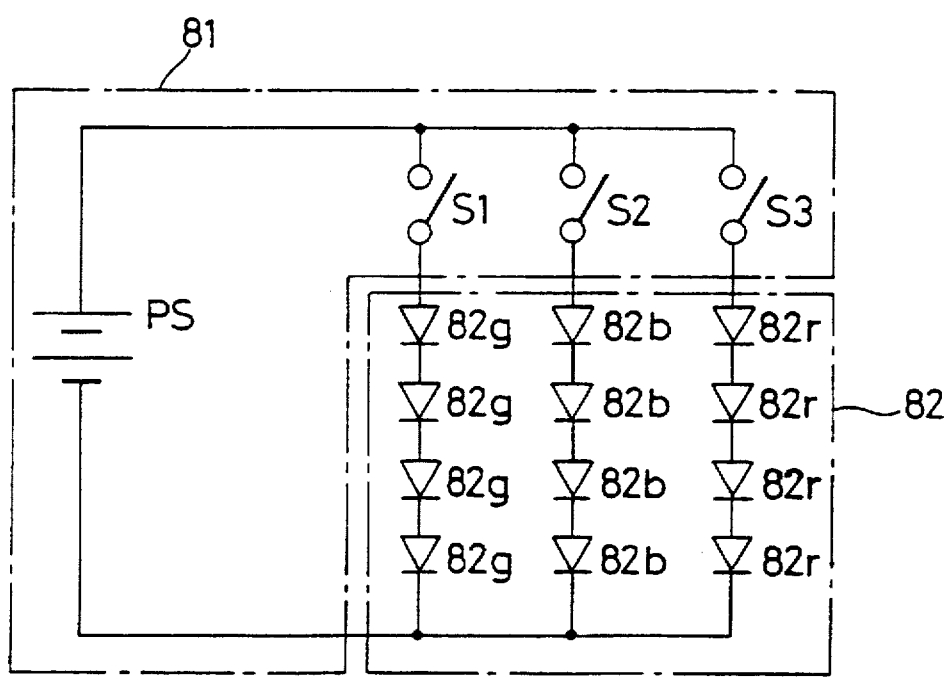
FIG. 26 is a view showing an electric circuit of an essential part of embodiment 5 of the present invention.

FIG. 26 is a diagram of an electric circuit showing a connection between the power circuit 81 and the LED 82. Electric current from the power supply PS is supplied to four green LEDs 82g by a switch S1, to four blue LEDs 82b by a switch S2, and to four red LEDs 82r by a switch S3, respectively, to selectively turn the LEDs of each color on and off.

When the LED 82 is turned on, the emitted light is directed via the ring-like mirror 34b and exits from the tip of the probe to illuminate the detection region V in the blood vessel 12 via the transparent plate 66 and the skin surface 16. The reflected light from the detection region V is received by the CCD 40a via the transparent plate 66 and the object lens 38b. The resulting captured images of the detection region V are then analyzed by the main body 20 of the analyzer to calculate the blood components in the same manner as in the above-described embodiments.

In order to determine oxyhemoglobin, either the switches S1 and S3 are turned on or the switches S2 and S3 are turned on, whereby the detection region V is illuminated with a 450 nm or 560 nm wavelength light and a 660 nm wavelength light.

Since oxyhemoglobin shows high absorptivity at around 450 nm and 560 nm and low absorptivity at 660 nm, oxyhemoglobin can be determined by analyzing the differential image obtained therefrom.

In order to determine bilirubin, the switches S1 and S2 are turned on, whereby the detection region V is illuminated with a 450 nm wavelength light and a 560 nm wavelength light.

Since bilirubin shows high absorptivity at around 450 nm and low absorptivity at 560 nm, bilirubin can be determined by analyzing the differential image obtained therefrom. Here, either a continuous irradiation or a pulse irradiation may be employed according to the needs.

Also, a diffusion plate may, if desired, be disposed in front of the LED to reduce illumination irregularities.

Embodiment 5 not only allows the dark-field illumination (see FIG. 23) as in embodiment 4 but also reduces the size of the apparatus because the illumination lamps are disposed around the object lens.

Further, since the light emitted from the light source is directly applied to the object, the emitted light is utilized more efficiently than in the case of embodiment 4, thus making it possible to employ a small light source.

Moreover, it is possible to carry out a quantitative measurement by selectively applying a light having a suitable wavelength corresponding to the absorptivity of an object for measurement, for example, hemoglobin and bilirubin, and by making use of the effect of ultraillumination.

According to the present invention, among the lights that are applied to the living body, the light reflected at the blood vessel (blood) to be measured is directed to the image capturing device, whereas the unnecessary light reflected at the skin surface does not reach the image capturing device, so that blood images can be obtained with a good contrast.

Further, the present invention enables non-invasively capturing, without collecting blood from the living body, an image of a predetermined volume of blood passing through the blood vessel and measuring the blood components by analyzing the image thereof. For example, the number of blood cells per unit volume can be counted. Also, the hematocrit value, hemoglobin, and red blood cell constants can be calculated. Furthermore, it is possible to classify white blood cells because the obtained images are clear despite the fact that they are non-invasively captured.

Disposing a plurality of light emitting elements around the object lens for light application can reduce the size of the apparatus.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A non-invasive blood analyzer comprising:

light application means for applying light to a detection region in a blood vessel contained in a part of a living body;

image capturing means, responsive to light reflected from said detection region, for capturing an image of the detection region from the reflected light; and analysis means for analyzing characteristics of blood components contained in the detection region by processing the image captured by the image capturing means, the image capturing means including a lens for converging the light reflected from the detection region, and the light application means applying light to the detection region at an incident angle larger than an aperture angle of the lens with respect to the detection region to provide dark-field illumination.

2. A non-invasive blood and analyzer according to claim 1 wherein the analysis means analyzes captured images of blood cells.

3. A non-invasive blood analyzer according to claim 1 wherein the image capturing means captures images of bilirubin in blood.

4. The non-invasive blood analyzer of claim 3, wherein the light application means illuminates the detection region with a blue and a green light to aid the image capturing means in capturing images of bilirubin in blood.

5. A non-invasive blood analyzer according to claim 1 wherein the image capturing means captures images of oxyhemoglobin in blood.

6. The non-invasive blood analyzer of claim 5, wherein the light application means illuminates the detection region with at least one light emitting element for emitting at least one of red, green and blue light.

7. The non-invasive blood analyzer of claim 6, wherein the light application means illuminates the detection region with a red light and one of a blue and a green light to aid the image capturing means in capturing images of oxyhemoglobin in blood.

8. A non-invasive blood analyzer according to claim 1 wherein the light application means comprises a plurality of light emitting elements disposed around the lens and light guiding means for directing light emitted by the light emitting elements to the detection region.

9. The non-invasive blood analyzer of claim 8, wherein the light application means includes light emitting elements for emitting red, green and blue light.

10. The non-invasive blood analyzer of claim 9, wherein the light application means illuminates the detection region with a red light and one of a blue and a green light to aid the image capturing means in capturing images of oxyhemoglobin in blood.

11. The non-invasive blood analyzer of claim 9, wherein the light application means illuminates the detection region with a blue and a green light to aid the image capturing means in capturing images of bilirubin in blood.

12. A non-invasive blood analyzer according to claim 1 wherein the light application means comprises a plurality of light emitting elements disposed around the lens, each of the light emitting elements emitting light of one of a plurality of different wavelengths, light guiding means for directing light emitted by the light emitting elements to the detection region, and control means for selectively energizing light emitting elements to emit light of different wavelengths.

13. The non-invasive blood analyzer of claim 12, wherein the light application means includes light emitting elements for emitting red, green and blue light.

14. The non-invasive blood analyzer of claim 13, wherein the light application means illuminates the detection region with a red light and one of a blue and a green light to aid the image capturing means in capturing images of oxyhemoglobin in blood.

15. The non-invasive blood analyzer of claim 13, wherein the light application means illuminates the detection region with a blue and a green light to aid the image capturing means in capturing images of bilirubin in blood.

* * * * *

UNITED STATES PATENT AND TRADEMARK OFFICE
CERTIFICATE OF CORRECTION

PATENT NO. : 5,791,345
DATED : August 11, 1998
INVENTOR(S) : Ken Ishihara, et. al.

It is certified that error appears in the above-identified patent and that said Letters Patent is hereby corrected as shown below:

Title page, item [30], under Foreign Application Priority Data, insert –

```
Sept. 3, 1993  [JP]  Japan......5-220147
Mar. 25, 1994  [JP]  Japan......6-056259
```

Signed and Sealed this

Eighteenth Day of May, 1999

*Attest:*

Q. TODD DICKINSON

*Attesting Officer*     *Acting Commissioner of Patents and Trademarks*